United States Patent [19]
Hay et al.

[11] Patent Number: 5,632,282
[45] Date of Patent: May 27, 1997

[54] OCULAR DISEASE DETECTION APPARATUS

[76] Inventors: S. Hutson Hay, 310 Clinton Ave. West, Huntsville, Ala. 35801; P. John Reiner, 108 Sunscape Dr., Huntsville, Ala. 35806

[21] Appl. No.: 324,884

[22] Filed: Oct. 18, 1994

Related U.S. Application Data

[63] Continuation-in-part of Ser. No. 93,685, Jul. 20, 1993, Pat. No. 5,355,895.
[51] Int. Cl.$^6$ .................................................. A61B 13/00
[52] U.S. Cl. .................................................. 128/745
[58] Field of Search .................. 128/745; 351/200, 351/221

[56] References Cited

U.S. PATENT DOCUMENTS

| | | | |
|---|---|---|---|
| 4,569,354 | 2/1986 | Shapiro et al. | 128/745 |
| 5,139,030 | 8/1992 | Seay | 128/745 |
| 5,303,709 | 4/1994 | Dreher et al. | 128/745 |

FOREIGN PATENT DOCUMENTS

| | | | |
|---|---|---|---|
| 9203084 | 3/1992 | WIPO | 128/745 |

*Primary Examiner*—Max Hindenburg
*Attorney, Agent, or Firm*—M. Clodfelter

[57] ABSTRACT

A method for diagnosing a plurality of disorders of optical media of the eyes is disclosed. A beam of light is directed into eyes of a subject, and the retinal reflection, or reflex, emerging from the pupil is detected and analyzed. In some instances intensity levels of the reflex are compared against a reference reflex representative of a normal eye to isolate abnormal ocular conditions, and in other instances the subject's reflex is divided into portions and comparisons made between selected portions to isolate abnormal ocular conditions. Additionally, binocular status is evaluated by examining the eyes simultaneously.

23 Claims, 18 Drawing Sheets

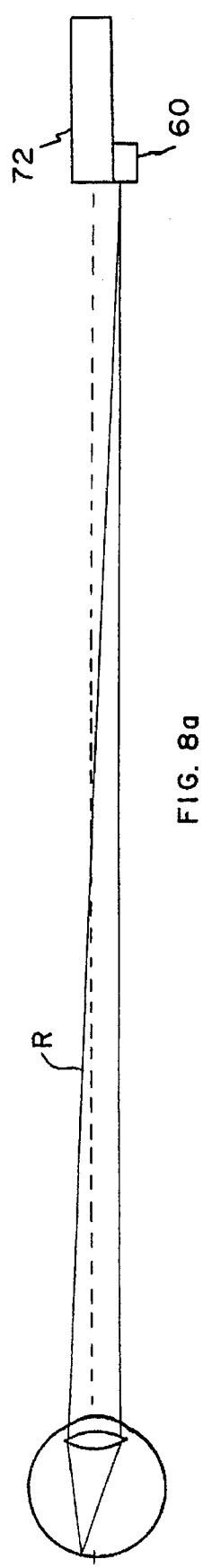
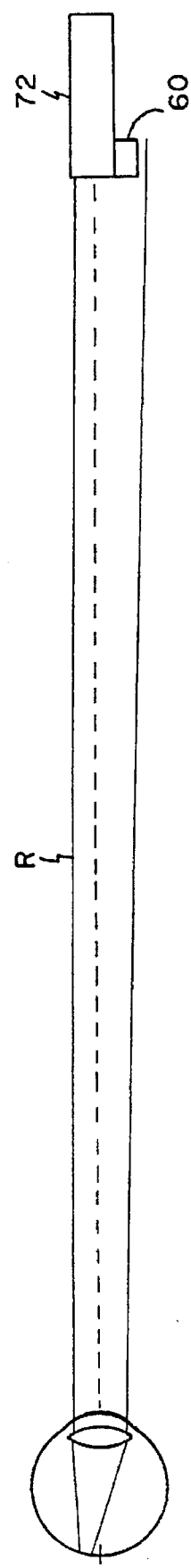
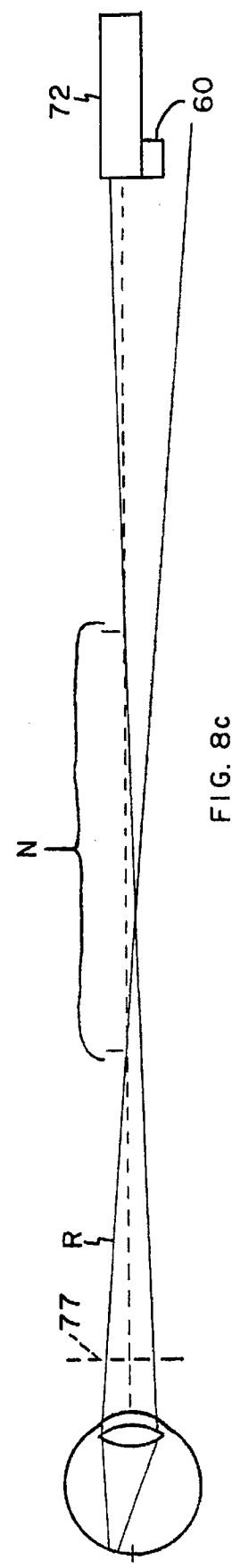
FIG. 8a
FIG. 8b
FIG. 8c

MYOPIA    HYPEROPIA

PUPIL ARRAY

OCULAR DISEASE DETECTION APPARATUS

CONTINUING APPLICATION DATA

This application is a continuation-in-part of application Ser. No. 08/093,685, filed Jul. 20, 1993, now U.S. Pat. No. 5,355,895.

FIELD OF THE INVENTION

This invention relates generally to devices for detecting optical ocular diseases in the human eye, such as those related to refractive error, opacities of the eyes, and alignment of visual axes of the eyes, and particularly to a compact, portable device of the stated type which defocusses eyes of a subject. This occurs through use of a first visual stimulus at a first focal distance, which also serves as a partially reflective surface, with a second visual stimulus at a second focal distance superimposed on the first visual stimulus. A beam-generating flash unit provides an adjustable beam of light to the eyes, and a CCD camera records an image of the eyes as reflected from the first visual stimulus. The image of both the eyes is provided to a computer, in turn provided with an analysis program that performs diagnostic analyses based on the image.

BACKGROUND OF THE INVENTION

In preschool children, detection of strabismus, a class of maladies characterized by deviation of the optical axis of one eye from the optical axis of the other eye, one such malady being commonly known as "lazy eye" (amblyopia), is particularly important. As an untreated child having one or more of these forms of strabismus becomes older, neural development in the brain tends to permanently suppress vision in the diseased eye. This prevents development of proper binocular vision in the child, with this impairment becoming irreversible after about two years of age. Thus, to correct this condition, treatment must begin in the early years of life to be effective. As about 5% of children are either born with or develop a form of strabismus, diagnosis and treatment of this condition at as early an age as possible, preferably prior to about 12 months, is highly desirable. However, considerable difficulty may be encountered in properly administering an ocular screening test to preverbal children of such a young age.

Additionally, other conditions of the eyes relating to errors of refraction of the transparent media of the eye, such as nearsightedness (myopia) and farsightedness (hypermetropia), and conditions relating to opacities of the eyes, such as cataracts, scars or foreign objects in the cornea, and tumors, as well as problems such as detachment of the retina, need to be diagnosed and treated to provide higher quality vision for the patient.

Screening devices for screening a large number of subjects over a relatively short period of time have been proposed for detecting strabismus and other abnormal conditions of the eyes. These devices function by directing light from a light source to the eyes of a subject, which are fixed and focussed at a point defined by a fixation light mounted about 1 degree off-axis with respect to the light source. Generally, a camera utilizing photographic film is positioned as close as possible to the fixation light. As such, off-axis light from the light source enters the eyes, and is refracted by the transparent media, which includes the lens, of each of the eyes.

In an individual with normal eyes, an incoming image of the light source is refracted, and perfectly focused as tiny image upon the retina. As the light is off-axis with respect to an optical axis of the eyes, the tiny image of the light source falls generally on the macula, a pigmented structure of the retina, and the fovea, which is coincident with the optical axis of the eyes. A portion of the incoming light is reflected, generating a retinal reflection, or reflex. This retinal reflection is re-refracted by the lens as it exits the eyes, and is collimated thereby to be directly coincident with respect to light from the light source.

In the individual with normal eyes, the camera records a small, well-defined point of light in the center of the pupil, this point being a reflection from the cornea, or outer transparent covering of the eye. The reflection from the macula is not seen due to the lens of the eye perfectly focussing the outgoing reflection and directing this focussed reflection axially back to the light source; however, faint illumination of the macula is observed around the reflection from the cornea due to scattering of light within the eye. This faint illumination of the macula with a small, centered reflection from the cornea is the optical signature of a refractively good and otherwise normal eye.

With the flash positioned above the camera lens and separated from the lens and fixation light by about one degree of angular separation, a nearsighted eye (myopia) refracts the outgoing reflection to be diverging and inverted, instead of being collimated. If the angle of divergence of the retinal reflection from the myoptic eye is large enough, then a portion of the retinal reflection is intercepted by the camera lens, which portion being characteristically in the shape of a crescent. As a result, the camera records a bright crescent from each eye generally in the lower quadrants of the pupil; the crescents appearing in the lower quadrants due to inversion of the retinal reflection effected by the myoptic eye. Of course, the distance between the subject and the flash, fixation light and camera determines sensitivity of the device, with a longer distance allowing greater divergence of the retinal reflection, meaning that a bright crescent will be recorded at lower errors of refraction of the eyes. Conversely, a shorter distance between the subject and the flash, fixation light and camera allows less divergence of the retinal reflection, causing the camera to record a bright crescent at higher errors of refraction of the eyes. Generally, and irrespective of the sensitivity of the device, the area of the pupil covered by the bright crescent is directly related to the degree of nearsightedness.

In the instance where the eyes are farsighted (hypermetropia), the retinal reflections diverge as described, but are not inverted prior to being received by the camera lens. As such, the bright crescents appear on the same side of the pupil as the flash with respect to the camera lens. Thus, with the flash located above the camera as described, the camera records a bright crescent in the upper quadrants of the pupil. Again, the area of the pupil encompassed by the crescents correlates directly with severity of the farsighted condition.

In the instance where an individual is afflicted by strabismus, the deviation of the optical axis of one eye with respect to the optical axis of the other eye, the point of light reflected by the cornea in the deviating eye is not equidistant from upper and lower and right and left sides of the eye, as compared with the non-deviating eye. Additionally, where the axial deviation of the deviating eye is generally in the direction of the camera lens, a portion of the retinal reflection may appear where the deviation is relatively small, or most or all of the reflection may appear where the deviation is larger. With respect to astigmatism, which is usually associated with nearsightedness or farsightedness, the crescents will be rotated around edges of the pupil in a positive or negative direction a number of degrees corresponding to the particular combination of the axis and optical power of the astigmatic eyes of that individual.

Opacities of the transparent media of the eyes, such as cataracts or scars on the cornea, or opacities of the lens, produce darkened regions in the reflections wherever they are located.

In some of these devices of the prior art, the fixation light is positioned about 18.9 feet from the subject, a distance such that when the eyes are focussed on the fixation light, the optical axes of the eyes are essentially parallel and focussed on optical infinity. At this distance, slight divergence of the retinal reflection corresponding to about 0.25 diopters refractive error of the eyes is recorded by the camera. However, size of these devices is a drawback; devices of this length are awkward to handle and move, and require a table or support of about 18.9 foot length when in use. Further, since these devices are very sensitive to refractive errors, children having only minor refractive error defects of from about 0.25 to about 0.5 diopters, and who may derive only dubious benefit from corrective lenses, were selected during screening as having defective vision.

Finding the length of these longer screening devices to be cumbersome to move and temporarily install, others have proposed reducing size of these devices by shortening the optical path between the camera, light source, and eyes of the subject. However, when eyes of a subject are focussed on a relatively near fixation light, the optical axes of the eyes converge on the fixation light, rotating the retinal reflection about the optical axes of the eyes and causing the appearance of an astigmatic condition. Further, normal convergence of the eyes on a relatively near fixation light may prevent differentiation of some ocular misalignment disorders.

One of these proposed screening devices is disclosed in U.S. Pat. No. 4,669,836, to Richardson et. al., and includes a foldable base which unfolded measures about 2.4 meters in length. At one end of the base is an upwardly extending head positioning station for positioning the head, and thus eyes, of an individual being screened in relatively precise vertical and horizontal planes. At an opposite end of the device is a camera focussed in a plane of the head positioning station. An electronic flash unit is mounted below the camera, and a blinking fixation light to draw the gaze of an individual is mounted just above the camera lens.

Problems with this device are, as stated, its length, which in spite of the fact that it may be folded for storage or transport, requires that it have in excess of 2.4 meters of unobstructed floor space. When folded, its mass is about 22 pounds. Further, since images of subjects eyes are photographically made on film, there is no immediate feedback as to whether eyes of the subject were correctly positioned, if the test was correctly administered, or if the subject was cooperative in looking at the fixation light, a requisite condition for obtaining a satisfactory screening result. Additionally, since the device is less than half the 18.9 foot length required for a subject to focus his/her eyes on infinity, optical aberrations are introduced in the recorded images due to the eyes converging on the fixation light. This impairs accuracy of the device. Further yet, the bright flash may startle very young children.

A screening device similar to that described in U.S. Pat. No. 4,669,836 is described in a paper entitled *THE REMOTE SENSING OF EYE DISORDERS UTILIZING THE RETINAL REFLEX PHOTOMETER* by S. Hutson Hay and Rhonda Wharry, which was published in volume 601, pages 107–111 of the 1985 *PROCEEDINGS OF THE SOCIETY OF PHOTO-OPTICAL INSTRUMENTATION ENGINEERS*, and discloses a device also having a camera and off-axis flash at one end, a fixation light closely proximate the camera, and a head positioning station located 18.9 feet distant at the opposite end of the device. The photographic images may be subjected to limited computer enhancement.

Problems with this device are its length, which requires more than 18.9 feet of unobstructed floor space during use. Additionally, as in the prior device, photographic images are recorded on film which must be developed before the results are obtained. Again, the bright flash may be uncomfortable for small children.

Another paper entitled *RETINAL REFLEX PHOTOMETRY AS A SCREENING DEVICE FOR AMBLYOPIA AND PREAMBLYOPIC STATES IN CHILDREN*, by S. Hutson Hay, MD, Joseph H. Kerr, Robert Rhea Jayrose Jr., PhD, James C. White II, and Michael Funke, which was published in the March 1983 edition of the *SOUTHERN MEDICAL JOURNAL*, discloses a handheld camera with a 1,000 mm telescopic lens, with an off-axis flash mounted below the lens. A light-emitting diode (LED) serves as a fixation light, and is mounted just above the lens. The subjects head is carefully stabilized 18.9 feet from the lens, and with the subject gazing at the LED, a photograph with simultaneous flash is taken.

Again, this device requires more than 18.9 feet of unobstructed floor space in order to perform the screening, and photographic images are recorded on film which must be processed in order to obtain a result, and the flash may disturb small children.

U.S. Pat. No. 4,989,968, to Howard L. Freedman, discloses a camera having an internal light path of about 1 meter, the light path being folded by mirrors. The camera utilizes a small, slit aperture and a light source positioned 0.5 mm from the slit aperture. Both the slit aperture and the light source are mounted in rotatable relation with the optical axis of the camera, so that they may be rotated through at least a 90 degree arc. A series of LED fixation lights, which may be red or any other color, are mounted just below the slit. Provisions are made to place two photographs on a single sheet of self-developing film. Further, a parallex aiming system is provided which projects two light images onto the forehead of the subject, and the distance between the subject and camera adjusted until the light images touch, indicating proper alignment and focusing. In use, two photographs are taken of a single subject; the second photograph taken with the slit aperture and light source rotated 90 degrees from a position used to take the first photograph. This allows observation and recording of two discrete meridians of refractive error juxtapositioned 90 degrees with respect to each other.

Problems with this device are that two photographs are required, increasing the probability that the second photograph will be incorrectly taken due to the subjects vision being disrupted by persistence of the image of the first flash. Additionally, the necessity of taking two photographs with accompanying bright flashes in relatively quick succession may cause problems with small children, who after being startled by the flash during the first photograph, may be somewhat less cooperative during the second photograph. Further, it is necessary for an operator of the device to be actively involved with precise focusing and positioning of the camera and rotation of the slit aperture and flash between photographs, this all making for a relatively complicated and trying procedure, especially when groups of very young children, such as in daycare centers, are being screened.

In addition to the aforestated problems of the prior art with respect to recording images of eyes of the subjects, as far as applicants are aware, only limited computer analysis of these images has been attempted. In general, these enhancements have been limited to magnification of specific parts of the eyes, such as the retina and blood vessels therein, so that problems associated with the retina may be evaluated. Additionally, Applicant is unaware of any computerized analysis programs that examine both eyes to evaluate quality of the binocular state of a subject. Further, Applicants are unaware of any attempts by others to develop computer processing of images of the retinal reflexes of the eyes to screen for a plurality of disease conditions of the eyes.

Accordingly, it is an object of this invention are to provide an ocular disease detection system which includes data processing of images of the retinal reflex in order to diagnose a plurality of diseased conditions of the eye. As a further object of the invention, the data processing includes identifying problems associated with the binocular state of the eyes. In addition, it is an additional object to provide indications of these diseased conditions on a real-time basis, the entire diagnosing process taking only a few seconds.

SUMMARY OF THE INVENTION

A method for analyzing retinal reflections of a subject is disclosed. A beam of light is generated, and directed into eyes of a subject. An image of the eyes is received, and pupils of the eyes and the retinal reflections therefrom located. Light intensity levels of the retinal reflections are analyzed to determine whether pathologic conditions are present, and results of the analysis are plotted and displayed.

BRIEF DESCRIPTION OF THE DRAWINGS

FIG. 8a is a diagrammatic view of the retinal reflection of an eye with no refractive error and relative position of a camera lens and light source of the present invention.

FIG. 8b is a diagrammatic view of the retinal reflection of a farsighted eye and relative position of the camera lens and light source of the present invention.

FIG. 8c is a diagrammatic view of the retinal reflection of a nearsighted eye and relative position of a camera lens and light source, and showing a null region.

FIG. 12b is a continuation of FIG. 12a.

FIG. 14b is a continuation of FIG. 14a.

FIG. 15b is a flowchart of a portion of the flowchart of FIG. 15a.

FIG. 15c is a continuation of the flowchart of FIG. 15a.

DETAILED DESCRIPTION OF THE DRAWINGS

This device detects and quantifies ocular diseases, particularly cataracts, refractive errors of a selected degree, retinal detachments, alignment disorders, focussing disorders, corneal disease processes and alterations of media clarity resulting from inflammation or infection. Additionally, macular disease processes that alter the reflective properties of the macula, such as degenerative conditions, infection, inflammation, and tumors of the macular structures are detected. Further, the instant invention may be used to assess adequacy of a prescription of corrective lenses.

As a beam of light is directed into eyes of a subject, an image of the resultant reflection travels along an almost identical path but in a reverse direction as the beam to an image recording and display device. Additionally, by particularly utilizing a beamsplitter and mirrors in conjunction with an image of a dim, indistinct varying light, such as a moving light, an image is presented to a subject that requires the subject to attempt to focus on two discrete visual stimuli at two different focal lengths. Here, a relatively broad, dark visual field in a first focal plane serves as a first, background stimulus, and upon which a second visual stimulus, such as the image of a moving light, is projected from a second, longer focal distance and reflected to the eyes. This causes the subjects eyes to become relaxed and defocussed, as though the subject were looking at a distant object, bringing optical axes of the eyes into approximately parallel relation and allowing the lens of each of the eyes to relax to its normal shape. As is well known, the ciliary muscles of the eye serve to thicken the lens in response to focussing at relatively near distances, while allowing the lens to relax to a thinner shape when focussed at relatively far distances. This allows the optical and physical length of the invention to be limited to a relatively short length without the results being affected by convergence of the optical axis of the eyes or focussing of the lens therein on a relatively near fixation light. Further, the device of the present invention may be used to compare focussing of the eyes at relatively far and near distances, and allows simultaneous evaluation of responses of the eyes at such distances.

Figure 1:
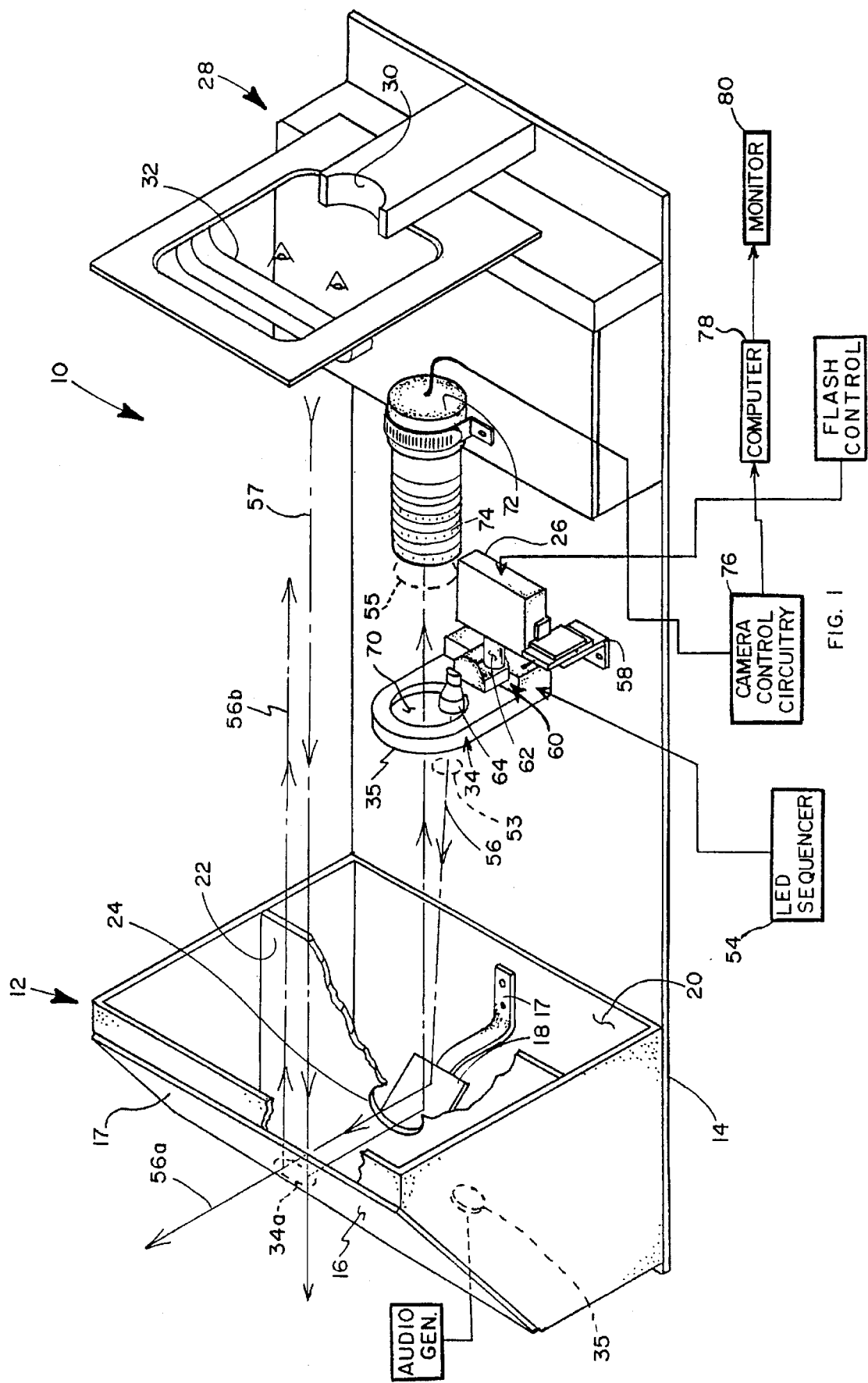
FIG. 1 is a partial pictorial, partial block diagram view of a first embodiment of the present invention.

Referring to FIG. 1, a first embodiment of an ocular diagnostic apparatus 10 of the present invention is shown. Here, an enclosure 12 mounted to a base 14 provides support for a beamsplitter 16, with a bracket 17 supporting a mirror 18 within a lower region of enclosure 12. Beamsplitter 16 is about 15 inches wide and about 12 inches high, and may be of a type of plate glass known as MIRROPANE EP (TM), manufactured by Libbey, Owen and Ford Inc. This type of glass is constructed having a darkly tinted substrate glass having one side coated with a reflective material such that about 60% of light striking the glass is reflected; the combination of the dark tint and reflective coating resulting in transmittance of visible light of about 13%. As such, with the reflective side oriented toward the subject, beamsplitter 16 provides a visual field of a flat, dark, featureless, relatively broad character.

Enclosure 12 is constructed having a generally open front region 20, with beamsplitter 16 mounted over and tilted toward mirror 18. This elevated relation of beamsplitter 16 over mirror 18 allows for construction of a more compact device due to folding of the optical path by mirror 18 and beamsplitter 16. Thus, for an ocular disease detection device having an effective focal length of 2 meters, or 78.75 inches, the device may be constructed of a shorter length of about 1 meter. It is to be noted that this length is the entire focal length of the device, and requires only little more than this length when in use. With this length, use of the device may occur in an area no larger than a small storage room or closet, as opposed to a larger area of something in excess of 18.9 feet, as required by at least some of the prior art devices.

A baffle 22 having an opening 24 for passing light and images therethrough is positioned between mirror 18 and beamsplitter 16, and is of a dark, nonreflective color, such as flat black, so as to absorb scattered light and prevent such scattered light from interfering with light reflected to and from beamsplitter 16. Additionally, baffle 22 assists in maintaining the flat, featureless visual character of beamsplitter 16 so that a subject looking at the beamsplitter focusses his/her eyes thereon. Beamsplitter 16 and mirror 18 are positioned as shown about 90 degrees with respect to each other, so that a portion of a beam of light or an image entering enclosure 12 and striking beamsplitter 16 is passed to mirror 18 and reflected out of enclosure 12, and a beam of light or an image entering enclosure 12 and striking mirror 18 is reflected to beamsplitter 16 and divided. This is also a feature of the invention, as a beam of light is generated by a flash unit 26, with only a portion of this beam, about 50%–60%, reflected by beamsplitter 16 to eyes of subjects being screened. As such, beamsplitter 16 reduces intensity of the beam directed into eyes of the subject.

Significantly, beamsplitter 16 is at a first distance, i.e. in a first focal plane, with respect to the subjects eyes, and receives an image of a small, moving light and reflects this image to the subjects eyes. Thus, the moving light is at a second, greater distance, i.e. a second focal plane, with respect to the subjects eyes. With the subject looking at the flat, featureless expanse of beamsplitter 16 at one focal distance and the projected image of the moving light superimposed on and reflected from beamsplitter 16 at a second focal distance, an optically confusing situation is created that temporarily defocusses the subjects eyes. This defocussing breaks convergence of the eyes and brings them into approximately parallel relation, and causes the ciliary muscles to relax, allowing the lens to assume its thinner, relaxed shape, as though the person were looking at something in excess of the focal length of the instant invention.

At the opposite end of base 14 about 38 inches from beamsplitter 16 is a positioning apparatus 28, which serves to position the head and eyes of an individual being screened in a particular focal plane of analysis. Positioning apparatus 28 includes a chinrest 30, which is conventionally adjustable by means not shown in order to vertically position the eyes within the area of the beam of light. A stabilizing bar 32 against which the subject places his/her forehead also assists in positioning and stabilizing the head, and thus the eyes, of the individual. Constructed as such, the subject has a relatively wide, unobstructed field of view, with beamsplitter 16 centrally located therein, which is unlike some of the prior art, which have small or narrow openings through which the subject is required to peer, causing subtle physiological changes to the eyes that alters accuracy of the device.

For producing an image of the small, moving light which is projected onto beamsplitter 16, and as another feature of the invention, a defocussing light apparatus 34 of annular construction is mounted to base 14 intermediate positioning apparatus 28 and enclosure 12 about 22 inches distant from mirror 18. With mirror 18 mounted about 8 inches below beamsplitter 16, an image of light from light apparatus 34 in a focal plane about 30 inches further than beamsplitter 16 is projected onto beamsplitter 16. As such, from positioning apparatus 28, with the beamsplitter at the first, shorter focal distance, the small, moving image from light apparatus 34 at a second, greater focal distance appears superimposed on beamsplitter 16. This combined image of the beamsplitter at one focal distance and a varying, or moving, light from light apparatus 34 at a second focal distance produces defocussing of the eyes, in contrast to the prior art which uses fixation lights to produce focusing and fixation of eyes of a subject at a particular focal length.

In some applications, as shown in FIG. 1, a second light apparatus 34 or other light emitting device may be mounted to the rearward side 17 of beamsplitter 16 at dashed line position 34a, so as to be in the same focal plane therewith. Here, the second light apparatus serves to provide a near fixation point upon which the eyes are focussed, for evaluating eyes focussed at the near fixation point. In this embodiment, two discrete images of the eyes are taken; one with the eyes defocussed by light apparatus 34 and beamsplitter 16 as described, and the other with the eyes focussed and fixed on the light apparatus at 34a. The two images of the eyes may then be compared to reveal any difference of refractive error between the defocussed and near focussed conditions. Tests thus far have revealed at least one young subject whose vision is close to normal when focussed at the focal plane of beamsplitter 16 (36 inches), but is substantially nearsighted when defocussed, as in a far focussed condition. While as yet undetermined, it is believed that the inverse condition is detectable, i.e. a condition wherein a subjects eyes are substantially normal when focussed at a far distance, but possess relatively higher refractive error when focussed at a near distance, such as the 36 inches or so to the second light apparatus at 34a. This may occur, for example, if the ciliary muscles were causing uneven thickening of the lens of one or both eyes or if thickening of the lenses were not commesurate with distance, and may cause reading difficulties or disabilities at early ages.

Figure 2A:
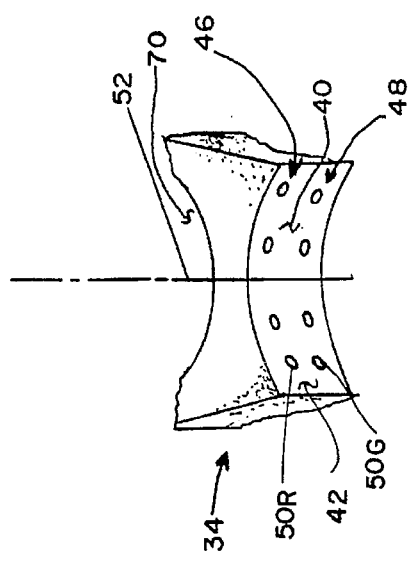
FIG. 2a is a pictorial view of a front and bottom region of the fixation light of the present invention showing relative positioning of LED lights.
Figure 2B:
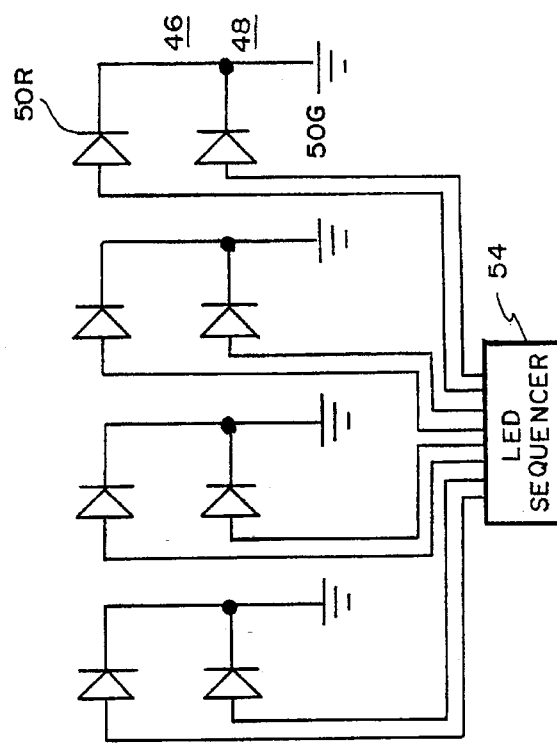
FIG. 2b is a schematic diagram of connections to the LED lights.
Figure 2:
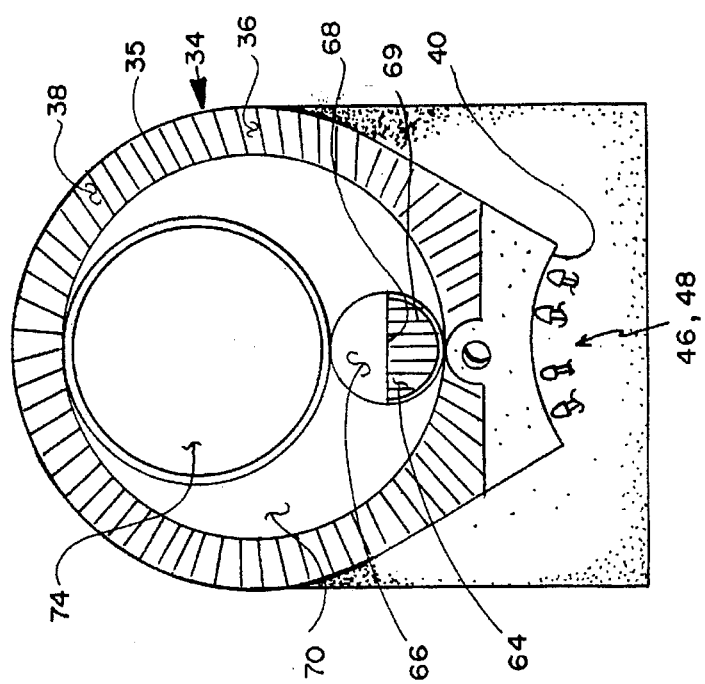
FIG. 2 is a planar view of a front region of a fixation light of the present invention which shows relative positioning of components.

In a preferred embodiment, and as shown in FIG. 2, defocussing light apparatus 34 may be constructed of a conventional ring flash 35, obtainable from most retail photography outlets. Ring flash 35 is provided with an annular light guide 36 about 3.5 inches in diameter having a circular interior region 70 of about 2.5 inches, with an annular, light emitting front region 38. This region 38 is generally configured to direct light outward from the interior of light guide 36 by a Fresnel (TM) or other similar type lens configuration. A light receiving window 40 (FIGS. 2 and 2a) at a bottom of ring flash 35 is provided with a cylinderically concave surface 42 having an axis 52 normal to a plane of the annular portion of ring flash 35, with window 40 adapted to receive light from a flash. Light received by window 40 is channeled to light emitting front region 38, where it is emitted in a forward direction therefrom. It is to be appreciated that a narrow beam of light directed at different positions of inner cylindrical surface 42 of window 40 results in the light emerging from front region 38 at different locations. For example, a small diameter beam of light directed about halfway down a side of window 40 results in a diffuse spot of light emerging about halfway down the same side of front region 38.

Accordingly, for purposes of this invention, and as shown in FIG. 2a, ring flash 35 is modified by locating two rows 46 and 48 of light emitting diodes (LED) positioned generally as shown by ovals 50R and 50G such that light from the LEDS is directed into window 40. Particularly, rows 46 and 48 are positioned normal to axis 52 of the cylindrical window 40, with row 46 consisting of LEDs 50R that generate light of red wavelengths, and row 48 consisting of LEDs 50G that generate light of green wavelengths. These colors are selected because nearsighted subjects are able to perceive light of the red wavelengths better than other colors, and farsighted subjects are able to distinguish the green wavelengths better than other colors.

The LEDs are illuminated by control circuitry 54 (FIG. 2b) in accordance with a repetitive pattern, such as a pattern wherein the LEDs of one of the rows are sequentially illuminated, and then the LEDs of the other row are sequentially illuminated. This may be accomplished, for example, by means of an octal binary sequencer that generates a repetitive binary code, with 8 discrete decoders that in turn each decode a one of the codes and provide power as an output to a respective one of diodes 50R and 50G. This results in diffuse spots of either red or green light which appear to travel around the front portion of ring flash 35, with spots of one color traveling around the ring, and then spots of the other color traveling around the ring. This type of moving light is believed to be particularly attractive and more intriguing to preverbal children, who otherwise may be uncooperative in looking at a single steady, or blinking, light. Additionally, it is believed that the apparent movement of the light serves to assist in defocussing the eyes by causing them to attempt fixation, which does not occur due to the optically confusing image of the beamsplitter at one focal distance and the moving light superimposed thereon at a second focal distance. Further, since intensity of light from each LED is relatively low, and is further diffused into a larger spot by the optical properties of ring flash 35, the spots of light that travel around ring flash 35 are quite dim, which also assists in defocussing the eyes by presenting relatively diffuse images having indistinct features. As such, the optical axes of the eyes are caused to be parallel, or nearly so, allowing differentiation of disorders related to ocular alignment from normal near convergence of the eyes.

Referring now to FIG. 1, and in addition to light apparatus 34, a source 35 (dashed lines) of audio stimulation, such as a piezoelectric buzzer or speaker coupled to an audio frequency generator, provides an audio stimulation that draws attention of the preverbal child, assisting the child in looking at the moving lights. Buzzer or speaker 35 is positioned behind beamsplitter 16 roughly in line with a center region of beamsplitter 16 and positioning apparatus 28, so that sound from buzzer or speaker 35 appears to be proximate the moving lights projected onto beamsplitter 16.

For illuminating the maculas of eyes of a subject being screened and providing a reflection therefrom, a slightly divergent beam of light 56 is directed onto mirror 18, which reflects the beam through opening 24 to beamsplitter 16. Beamsplitter 16 in turn reflects a relatively low intensity beam of light 56b to the subject being screened, and passes a portion 56a of beam 56 out of enclosure 12. This assists in preventing an uncomfortable, intense beam of light from impinging eyes of the subject, who may be a preschool child easily startled by an intense flash of light from a photographic flash.

Beam 56 is generated by an electronic flash unit 26 mounted to base 14 by means of an adjustable mount 58 positioned behind annular fixation light 34. Flash 26 provides a flash of light similar to a conventional photographic flash, the flash being of a duration of from 0.01 to 0.001 seconds. For forming and collimating the light into beam 56, a telescopic lens system 60, such as part number 516, available from TASCO, inc, is fixedly mounted to flash 26 so that an eyepiece 62 of the telescopic lens system receives light from flash 26, with the beam emerging from objective lens 64. This further reduces intensity of the flash, as a relatively small portion of light from the flash actually enters the smaller eyepiece lens, and is diffused further as it exits the larger objective lens. Further, lens system 60 is adjustable so as to vary its focal length, which produces a beam which is converging, diverging, or collimated, allowing reconfiguration of the instrument. Normally, for screening purposes, lens system 60 is adjusted to produce a diverging beam, which diverges to about 10 inches or so in diameter over the 2 meter focal length of the device, and which further diffuses light from flash 26. Alternately, the objective lens may be positioned to receive light from flash 26, with the beam emerging from the eyepiece. Here, with this reversed configuration, lens system 60 produces a more divergent or convergent beam, allowing the flash and lens system to be located closer to eyes of a subject. This may occur, for instance, where the flash is mounted to direct a beam directly to beamsplitter 16. In this instance, the intensity of light of the beam would be marginally greater than an intensity of light of a beam of the prior described orientation. However, this may be advantageous inasmuch as two discrete illumination levels of the eyes is available with this device. Further, wavelengths of the beam may be altered by positioning color filters, as shown by a dashed line position 53 of a filter placed in front of objective 64, to filter various wavelengths from the beam. This may be done, for example, to accurately define cataracts by using a beam of blue wavelength light, the cataracts preferentially absorbing light of such wavelengths. Further yet, polarizing filters may be used, such as a pair of circularly polarizing filters, such as a polarizing filter at position 53 and a second polarizing filter at dashed line position 55 in front of lens 74. Here, polarized light may be filtered by appropriately rotating the polarizing filters.

The beam of light formed and focussed by telescopic lens system 60 is directed through a lower portion 70 of annular fixation light 34, as shown in FIG. 2. Thus, when an individual places his/her head in positioning apparatus 28 (FIG. 1) and looks at the reflected image of the moving light from light apparatus 34 from beamsplitter 16, beam 56, when flash 26 is activated, covers about a 10 inch diameter area of analysis which includes the persons eyes and face.

Mount 58 supporting flash 26 is adjustable in fine increments in both horizontal and vertical directions, so as to precisely position flash 26 within a range of angular separation of about 0–5 degrees with respect to an optical axis of camera lens 74. This allows adjustment of the angular separation between flash 26 and the camera, which adjusts sensitivity of the device by reducing or increasing angular separation between the flash and the camera lens so that the lens receives a retinal reflection of lessor or greater divergence, respectively. Also, mount 58 may be adjusted so as to tilt flash 26, which in this case may direct a small-diameter beam of light which converges with the axis of lens 74 of camera 72 on eyes of the subject. This feature is used where it is desired to direct the beam directly into eyes of the subject with no angular separation between the light source and the flash, which is useful in diagnosing cataracts or other opacities of the transparent media of the eyes. While flash 26 and lens system 60 is shown in this embodiment to be mounted intermediate positioning apparatus 28 and camera lens 74, it is to be appreciated that the flash and lens system may be mounted at any point in the optical path between the positioning apparatus and lens 74, and may be mounted behind lens 74 as long as beam 56 is almost coaxial with a reflected image ray 57 of eyes of a subject.

For providing a reference for detecting astigmatism and further blocking a portion of the light of beam 56, (FIG. 2) an upper portion of objective 64 is blocked by an opaque material 66. In a preferred embodiment, about half of the objective is blocked, as by a razor blade, with a straight edge 68 of the blade extending horizontally across the central region of objective 64. While a horizontal edge is shown, edge 68 may extend vertically or diagonally in any reference plane, or edge 68 may be configured in a shape other than a straight edge. Additionally, horizontal edge 68 may be used in conjunction with vertical edges or lines 69, such as those found in a Ronchi rule, which may be obtained from Edmund Scientific Co. of New Jersey. This Ronchi rule is similar to an optical grating, and has about 50–100 vertical lines per inch. In this use, analysis of the retinal reflex using vertical and horizontal lines or edges is provided. Significantly, as shown, edge 68 provides a horizontal reference which may be detected in the retinal reflection, allowing a diagnosis of astigmatism and relative degree thereof to be made. Further, the opaque portion of material 66 blocks about half the light passed through telescopic lens system 60. This further reduces intensity of the light directed into eyes of the subject being screened. Further yet, while intensity of the device is described above to be adjustable by varying the beam 56 with respect to image ray 57, sensitivity of the device may also be adjusted by raising or lowering edge 68, which in turn varies angular separation of the beam from edge 68 with respect to image ray 57.

A charge coupled device (CCD) camera 72 (FIG. 1), such as a Model ST-4 Star Tracker imaging camera, available from Santa Barbara Instrument Group, 1482 East Valley Road, Suite 601, Santa Barbara Calif., and provided with a 55 mm, F1.28 telephoto lens 74, is also mounted to base 14. As stated, lens 74 is generally positioned slightly off axis from about 0–5 degrees above telescopic lens system 60, and receives an image through an upper region of annulus 70. By recording an image of the eyes through the annulus of the light apparatus, it is assured that the eyes are fixed directly on the camera lens without the necessity of placing a light directly on the optical axis of the camera lens, which would obscure a portion of the reflection from the eyes.

The CCD camera is particularly sensitive to light, and has an ASA rating of about 20,000, which is far more sensitive than any of the photographic film of the prior art. As such, the faint reflection from the retina and reflection of the cornea is easily observable, and may be obtained from the relatively dim beam 56 which does not evoke a startle reaction from the subject. While lens 74 and camera 72 are shown mounted above telescopic lens system 60, the camera and lens thereof may be positioned on any side of telescopic lens system 60, as long as the camera receives an image of the eyes through the annulus of the ring flash.

Control circuitry 76 is coupled to a monochrome camera 72, and is provided with software adapted to control outputs from the picture elements (pixels) of the CCD sensing element of the camera. In a prototype device, camera 72 is provided with a focal plane array comprising 192 columns of pixels and 165 rows of pixels, although larger focal plane arrays having more pixels may be utilized in order to obtain higher resolution of the data. Additionally, the pixels of the array may be arranged in other configurations than rows and columns, such as a circular array. Further, while camera 76 uses a monochrome focal plane array wherein each pixel provides 256 graduations of gray, or a grayscale of 256, it is believed that some disease processes, such as cataracts, may be more easily analyzed by utilizing a camera having a focal plane array responsive to radiation in either the ultraviolet spectrum or infrared spectrum, or combinations thereof.

Control circuitry 76, when eyes of a subject are imaged, conventionally utilizes a frame grabber to store a video frame of the image of the eyes, digitizes the image, and provides it as a digital representation to computer 78. Computer 78 in turn stores the digital representation of the eyes in a file and gives the file an identification code. At this point, the digital representation of the facial area surrounding eyes of a subject is in the form of a bit map wherein position of each discrete pixel in the focal plane array is represented by a position in the bit map of an eight bit binary segment of code known as a "byte", with a value of each byte representative of a particular level of intensity of light registered by that pixel. As there are eight bits to a byte, there are 256 possible values of light intensity represented, with 0 being totally dark and 255 being the brightest intensity of light registerable by the pixels.

As an option, the bit map may include bright reference information from a first group of pixels that consistently receive light from a small, reflective surface 200 (FIG. 9a) mounted in the same focal plane as eyes of the subject, as by attachment to a forward facing region of chinrest 30, 102, (FIGS. 1, 7) in order to be consistently registered by the same pixels in the focal plane array. Surface 200 may simply be a small flat mirror or portion of reflective foil or the like, or it may be a concave mirror having a focal length so as to focus reflected light back to camera 72, insuring that a focused reflection therefrom will be the brightest reflection received by the focal plane array in camera 72. As such, the reflection from bright reference surface 200 will generally be the brightest reflection in the field of view, and will have an intensity value of about 100 or greater, depending on the optical response of the apparatus at any given time, as will be further explained.

As a further feature of this option, dark reference data is provided by a second group of pixels that consistently receive light from a highly non-reflective surface 202 mounted on the chinrest adjacent surface 200 (FIG. 9a), and which may be a light scattering surface, such as a Ramian backscattering surface, or a light absorptive surface that simply absorbs incident light. Pixels imaging this dark reference surface will typically have intensity values in the range of about 20 or less. As the ratio of reflectance between the bright reference surface and the dark reference surface is constant, information from these pixels may be used in a calibration capacity by scaling intermediate intensity values to these brightest and darkest intensity values, preserving the ratio therebetween and eliminating inaccuracies due to accumulations of dust on optics of the system, minor variances in intensity of the flash, and variations in sensitivity of the focal plane array.

While the bright and dark reference surfaces are disclosed as being mounted to the chinrest, they may be mounted anywhere in the optical path of the device so as to be consistently imaged by the camera.

After the data containing the bit map of the subjects eyes is parsed into a file, which may be stored in conventional nonvolatile memory for retrieval and examination at a later time or placed directly into RAM memory of the computer, a routine in computer 78 is called to generally locate pupils of the eyes, and provide the results graphically to monitor 80 for confirmation by the user that the eyes have been located. This routine, and the ones that follow, due to the linear nature of computer instructions and operation, is caused to operate first on one portion of the field of view containing one eye, and then the routine is caused to operate on the other portion of the field of view containing the other eye.

Figure 9:
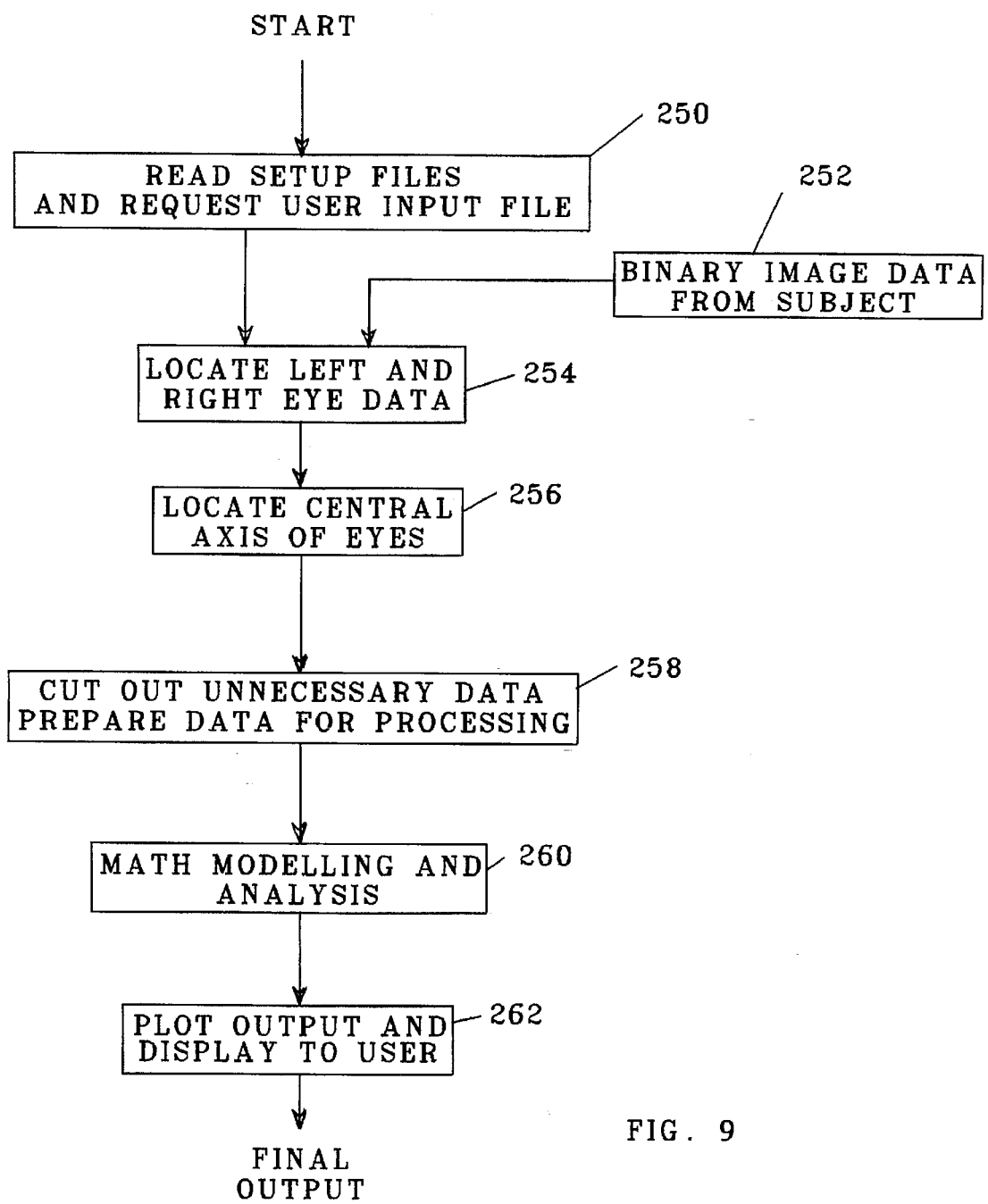
FIG. 9 is a high level flowchart of a program of the present invention.
Figure 9A:
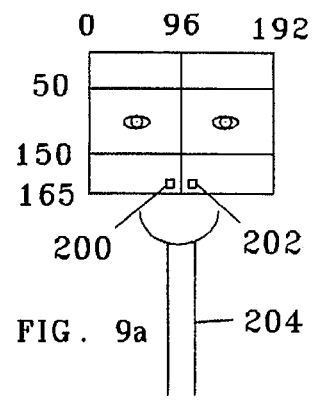
FIG. 9a is an illustration of a field of view from a camera of the present invention showing certain details therein.

Referring initially to FIG. 9, a flowchart illustrating overall organization of one embodiment of the program, at box 250 the setup files and initialization processes are loaded and implemented in computer 78. Input files are requested at box 252, which are either provided from memory storage media, or directly from control circuitry 76 (FIG. 1, 7), and which contain eye data from a subject. At box 254, the user or a routine in the program locates the left and right eye data, and another routine at box 256 locates the central axis of the eyes of the subject. Unnecessary data may be cut out at box 258, and math modeling and analysis is undertaken at box 260. At box 262, the results are plotted and displayed graphically to the user.

Figure 10:
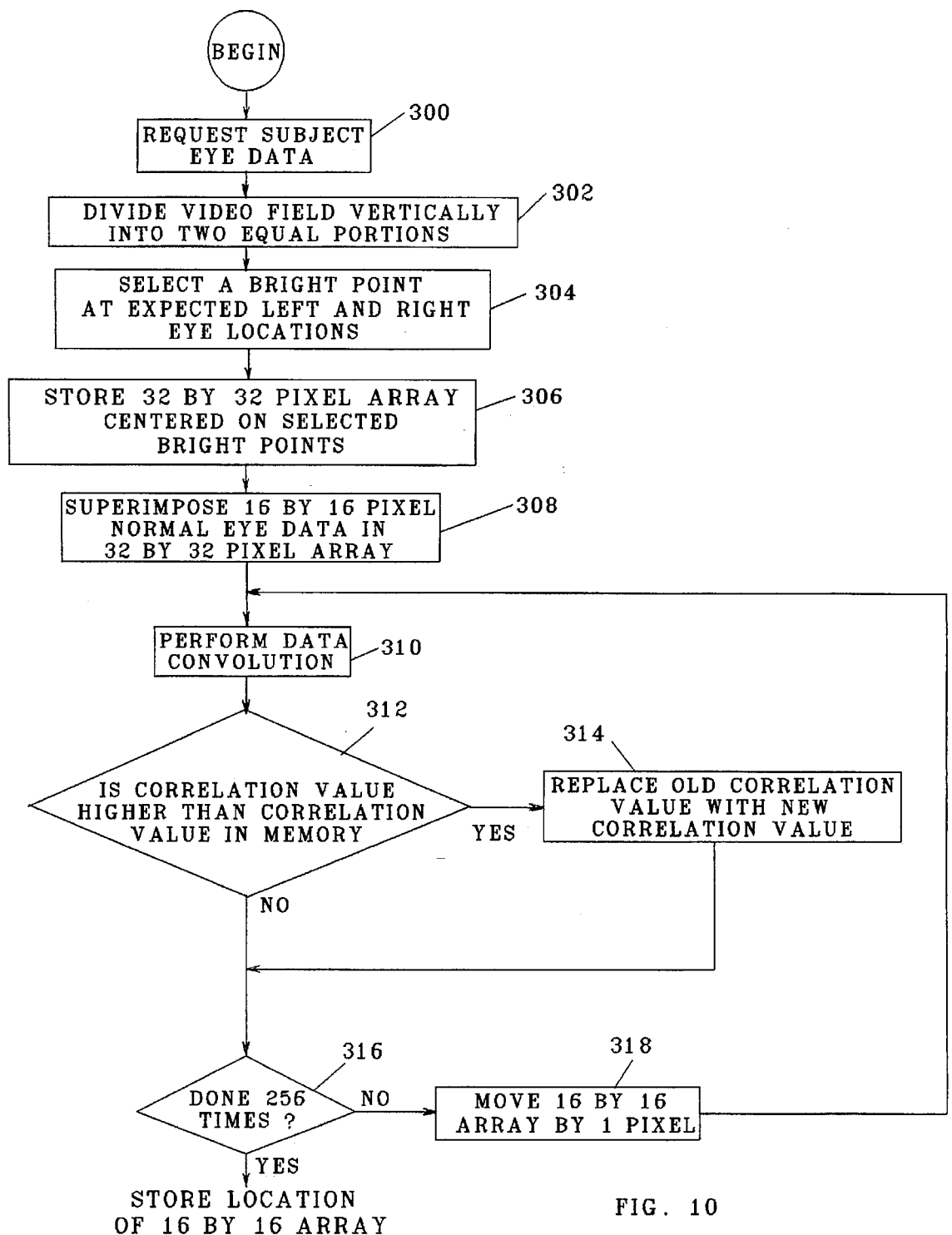
FIG. 10 is a flowchart of a method for locating pupils of eyes of a subject.

For a discussion of the flowchart of FIG. 9 in more detail, and in accordance with a preferred embodiment of the logic used to analyze the data from control circuitry 76, this embodiment set forth herein by way of example, reference is made to FIG. 10. Here, after the data processor is initialized and loaded with the operating system, which may be DOS 3.0 or better, and the eye analysis program, which may be written in Fortran or another suitable programming language, as determined by those skilled in the art, the user is requested at block 300 to provide the file containing the bit map including the subjects eyes as provided by control circuitry 76. This bit map, in addition to an image of the right and left eyes, includes an image of the nose, forehead, other superfluous data, and may further include images of the bright and dark calibration surfaces 200 and 202, respectively. As stated, and where used, the ratio of reflectivity between these reference surfaces does not change from one image to the next, thus providing a reference to compensate for drift of light intensity between discrete images from the factors as described above. In addition to a calibration function, the reference surfaces are useful to ensure tracking of optical degradation of a subjects eyes, as where progression of a cataract is being monitored, by eliminating the effect of variance of intensity of light recorded by the device, and drift of response of the flash and focal plane array.

At box 302 of FIG. 10, the video field, which is composed of 165 rows of pixels and 192 columns of pixels, is vertically divided into two equal portions of 96 columns each, with the vertical division line centered on support 204 (dashed lines in FIG. 9a) of the chinrest. This assures that the right and left eyes of a subject will appear in respective left and right portions of the video field. Additionally, this allows the left and right eyes to be treated separately for analytical purposes. If desired, upper and lower regions of both portions, which virtually never contain eyes of a subject, may be excluded from data processing by only considering image information between selected rows of pixels where eyes of a subject are most likely to appear, such as between rows of pixels 50 and 150. This reduces the possibility of an error due to reflections from facial areas around the nose and forehead, and also reduces computational overhead by reducing the area which must be examined, as will be further explained. Next, at box 304, the right and left portions of the video field are each scanned for the corneal reflection by looking for a small group of pixels on the order of 2–5 pixels which register highest intensities of light in that portion of the video field. The corneal reflection is generally brighter than other reflections within or around the eye due to the fact that the reflection from the cornea has not made any transitions through the transparent media of the eye, and typically has correspondingly higher digital values, on the order of 50 to 70, than other reflections in the video field. However, in some instances, larger areas of reflection, such as shiny areas of skin, some types of jewelry, etc, may generate reflections of similar intensities as the corneal reflection. For eliminating these other areas of reflection from consideration during scanning of the video field, a simple thresholded LaPlace filter, which is sensitive to and locates sharp edges in the image by performing a second derivative of the intensity value, as is well known to those skilled in the art, may be utilized to limit size of the selected groups of pixels to 2–5 pixels or so. As such, only small groups of pixels having highest digital values are selected as indicating probable location of the corneal reflection.

Figure 9C:
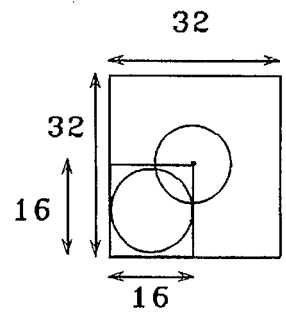
FIG. 9c is an illustration of a 16 by 16 pixel normal pupil array superimposed in the array of FIG. 9b.
Figure 9B:
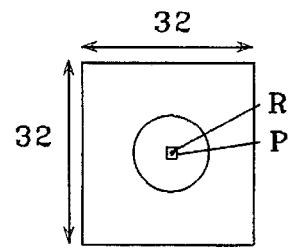
FIG. 9b is an illustration of a 32 by 32 pixel array containing a pupil of the subjects eye.

At box 306, and as shown in FIG. 9b, an array of 32 by 32 pixels square is located about a probable corneal reflection R in each portion of the video field. Here, the 32 by 32 pixel array is built and centered about a pixel P registering the highest intensity of the corneal reflection, this pixel being located at row 16 and column 16 of the 32 by 32 pixel array, with this pixel referencing a center point of the array. By utilizing an array of 32 pixels square for each eye, it is assured that the pupil, which typically occupies an area of about 16 pixels square, will be imaged in those cases where the corneal reflection is shifted due to strabismus or other disorders. Additionally, by selecting a 32 by 32 pixel array centered about the corneal reflection, it is assured that the eyes of a subject are analyzed together in binocular relation in the same focal plane while excluding irrelevant features in the video field, such as jewelry, from further consideration.

At this point, color enhancement may be added as will be further described, and the 32 by 32 pixel arrays may be displayed on the monitor for confirmation by the operator that the pupils have been located, who would then initiate further processing. If the eyes have not been located within the 32 by 32 pixel array, which may occur due to selection of a bright reflection from the eye that is not a corneal reflection, such as an inflamed tear duct, then the operator instructs the program to look for the next brighter points and form a 32 by 32 pixel image around these points and present them for confirmation. As a last resort, control of the computer may be passed to the user, who then may manually position a cursor at the corneal reflection, as by selected keys on the keyboard or an interface device, such as a mouse, and instruct the program to center the 32 by 32 pixel array at the pixel identified by the cursor. Significantly, as described in the foregoing, the pupils of the subjects eyes, even with normal eyes, provide a slight illumination as compared to the surrounding area in the 32 by 32 pixel array due to scattering and reflection of light within the eye from flash 26. At this point, the 32 by 32 array containing the pupil is stored for analysis.

As an optional mechanism for locating the pupils, after the pupils are located within the 32 by 32 pixel array, either manually or automatically, and as shown by box 308, the pupils of a subjects eyes may be located by comparing the subjects eyes with an image of a normal eye pupil, and determining a "best fit" of the subject pupil with the normal pupil. This normal pupillary image, which is centered in a 16 by 16 pixel array, is obtained by averaging the pupillary image from a number of subjects having eyes considered to be normal as determined by clinical evaluation, and includes a well defined, circular pupillary opening uniformly illuminated as described with a bright corneal reflection centered therein. Due to illumination within the eye as seen from the pupil, corners of this 16 by 16 pixel array which image portions of the iris appear darker than the pupil.

This comparison process of box 308 begins by superimposing the 16 by 16 pixel array of the normal pupil in one quadrant of a 32 by 32 pixel array containing the subjects pupil, as shown in FIG. 9c. A data convolution, as indicated in box 310, is then performed between the corresponding pixels of the quadrant of the 32 by 32 pixel array and the 16 by 16 pixel array of the normal pupil. This data convolution is done by multiplying intensity values of pixels in the 16 by 16 pixel array of the normal eye by intensity values of respective pixels in the quadrant of the 32 by 32 pixel array covered by the 16 by 16 pixel array. The results of these multiplications are then summed, with the degree of correlation between the 16 by 16 pixel normal pupil array and the quadrant of the 32 by 32 pixel subject eye array covered thereby being in direct relation with respect to this sum. This is because, except for pixels in each corner region, the 16 by 16 pixel array averaged from normal eyes is mostly occupied by the pupil, which emits the faint illumination as described above, with the corner pixels of this array registering a darker reflection from the iris. As such, in those instances where the normal pupil of the 16 by 16 array is not aligned with the subject pupil, then a lower correlation value will result due to a lower resulting value when the higher pixel intensity values of the normal pupil are multiplied by the lower intensity pixel values representative of darker areas around the pupil of the subject. In contrast, the highest correlation value is obtained when the normal pupil of the 16 by 16 pixel array is centered over the subject eye pupil, where the higher intensity values of the normal eye pupil are multiplied by the higher intensity values of the subject eye pupil.

After the first data convolution is performed in box 310, the inquiry is made at box 312, as by comparing a value of the correlation function currently obtained with a prior obtained correlation value stored in a portion of RAM memory, as to which of these correlation values is higher. With the memory initialized to LOW logic states, the first correlation value is always higher, causing the initial LOW value stored in memory to be replaced by the first correlation value, as indicated at box 314. Additionally stored in memory with the first correlation value is location of the 16 by 16 normal pupil array within the 32 by 32 array of the normal eye data, which location may be stored by simply storing location of a pixel in the 32 by 32 pixel array of the subject eye corresponding with the current location of the center pixel of the 16 by 16 normal eye array, which as stated is at the intersection of the eighth column and eighth row, so that the location of the subjects pupil within the 32 by 32 pixel array may be retrieved and further analyzed. After the first correlation value is stored, the inquiry is made at box 316 if the process has been repeated 256 times, as by counting the number of iterations as they occur, and if the requisite number has not occurred, then the program proceeds to box 318. Here, the 16 by 16 pixel array containing the normal eye is shifted by one pixel in the 32 by 32 pixel array from the subject, either across or up, and the program loops back to again perform the data convolution of box 310 with the normal eye array superimposed over a slightly different quadrant of the subject eye array. This yields a new correlation value which is compared with the prior-obtained correlation value from the prior data convolution, with a current, higher correlation value replacing a lower correlation value stored in memory. After repeating this process 256 times, the number of iterations necessary to shift the 16 by 16 pixel array to all possible positions within the 32 by 32 pixel array, the correlation value, or location of a center pixel in a particular 16 by 16 pixel array, remaining in memory indicates position of a 16 by 16 pixel array in the 32 by 32 pixel array from the subject having a highest correlation with the 16 by 16 pixel array of the normal eye. Where the final correlation remaining in memory after 256 iterations of this process is still low, as where the pupil is not fully located within the 32 by 32 array, suggesting that the initial placement of the 32 by 32 pixel array was not on the corneal reflection, then the 32 by 32 pixel array may be shifted, as by reinitializing the 32 by 32 pixel array to a different position, and repeating the process of FIG. 9. Typically, in an effort to locate the corneal reflection, the 32 by 32 array is first shifted to the left and then to the right, and then up and down until the corneal reflection is located as described.

Alternately, instead of comparing the normal eye array of 16 by 16 pixels with every possible position in a 32 by 32 pixel array that most likely contains the pupil of the subject, small, bright reflections in each portion of the video image may be selected as described at box 304, and the 16 by 16 array representative of the normal eye centered thereover. The convolution may then be performed to determine a correlation value which may be compared with other correlations obtained from positioning the 16 by 16 pixel array over other small, bright reflections, and the 16 by 16 pixel position indicated by the highest correlation value selected for presentation to the user for confirmation and further analysis. .

As in the instance where the corneal reflection cannot be located, or alternately where there is no algorithm for automatically locating the corneal reflection, the user may be prompted to manually position the 16 by 16 pixel array containing the normal eye data over the pupil of the subject eye by using selected keys on the keyboard or an interface device such as a mouse, as described earlier.

While the preferred methods are particularly described in the foregoing, the salient feature embodied therein is the identification of location of an array of pixels for each eye, each array containing a pupil of the subject.

Figure 11:
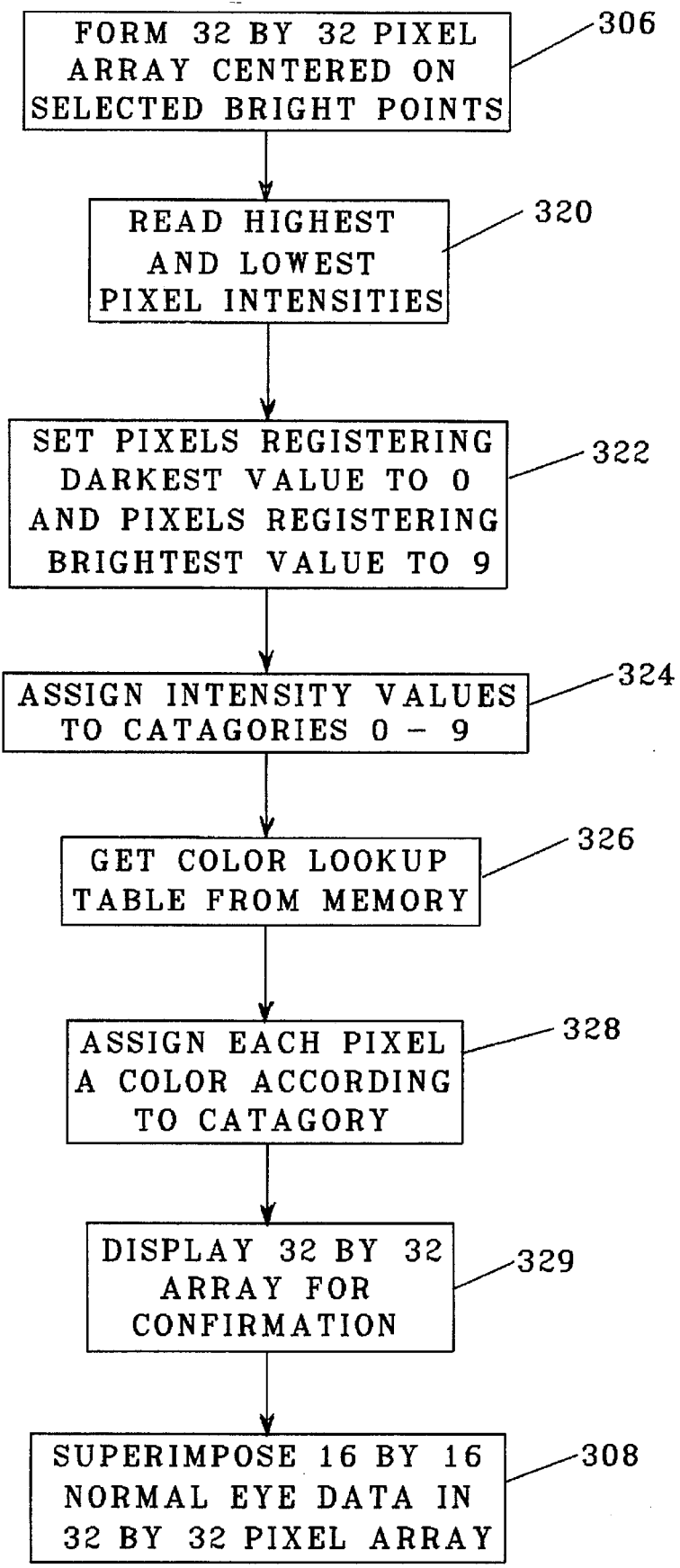
FIG. 11 is a flowchart showing a method for providing false color to the image of the subjects eyes.

In FIG. 11, a method of providing color enhancement to the video field is shown. In this method, the enhancement may be applied to the entire video field from camera 72, or only to the pixels in the 32 by 32 array. Additionally, while color enhancement may be applied at almost any point in the program, or left out entirely, it is preferable that the enhancement be applied prior to the first user interface, as shown at box 329, such as where the selection of a 32 by 32 pixel array may be presented to the user for confirmation that the eyes have been located using the corneal reflection, so that the enhancement is viewable at this point. As such, and as shown in FIG. 11, the color enhancement routine is placed, by way of example, between boxes 306 and 308 of FIG. 10. Here, and referring to box 320 of the flowchart of FIG. 11, the first step is to scan the 32 by 32 array for pixels registering the highest and lowest intensity values from the file containing the eye data. Alternately, the bright and dark surfaces 200 and 202 may be read to obtain these values.

Next, at box 322, the intensity value of pixels registering the darkest intensity are set to a lowest scaling value, such as 0, and pixels registering the brightest intensities are set to a highest scaling value, such as 9. Intermediate intensity values registered by pixels receiving the eye data are then scaled between scaling values of the darkest and brightest intensities. By way of example, in a typical image of a subjects eyes, the darkest pixel may register an intensity value of approximately 20 or so, and the brightest pixel registering the corneal reflection may register an intensity value between 60 and 70, with pixels imaging the area around the eyes thereof registering values between about 30 and 65. With this range of intensity values, discrete categories of intensity values may be established, as shown at box 324, which categories being linearly scaled between 0 and 9. As such, intensity values from about 20–23 may be assigned a scaled value of 0, intensity values 24–26 may be assigned a scaled value of 1, intensity values from about 27–30 may be assigned a scaled value of 3, and so forth. A color lookup table which lists a unique color for each category of intensity is then retrieved from memory, as indicated by box 326, and a unique color is assigned to each category of intensity values, as shown at box 328. Thus, pixels registering an intensity value of from about 20–23 may be assigned a color of blue, pixels registering between about 24–26 may be assigned a color of red, pixels registering between about 27–30 may be assigned a color of yellow, etc. Where the bright and dark reflective surfaces are used, and due to the ratio of reflectance between the dark reflective surface 202 and the bright reflective surface 200 being constant, factors that affect transmissivity and reception of light in the apparatus, such as varying or drifting response of the focal plane array, accumulations of dust on the lenses and mirrors of the apparatus, or drifting of the output of flash 26, do not change the false colors applied to the image. This feature is important in tracking changes of clarity of eyes of a subject between images taken at selected intervals, as where progression of a cataract is being monitored.

Figure 12D:
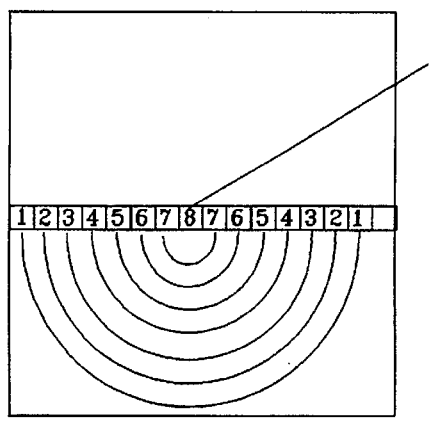
FIG. 12d is an illustration of a conical mask of the method of the present invention.
Figure 12C:
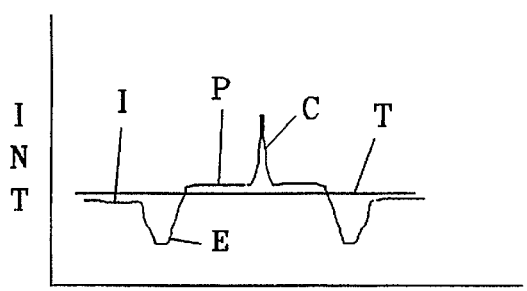
FIG. 12c is a plot of intensities of a normal eye.
Figure 12A:
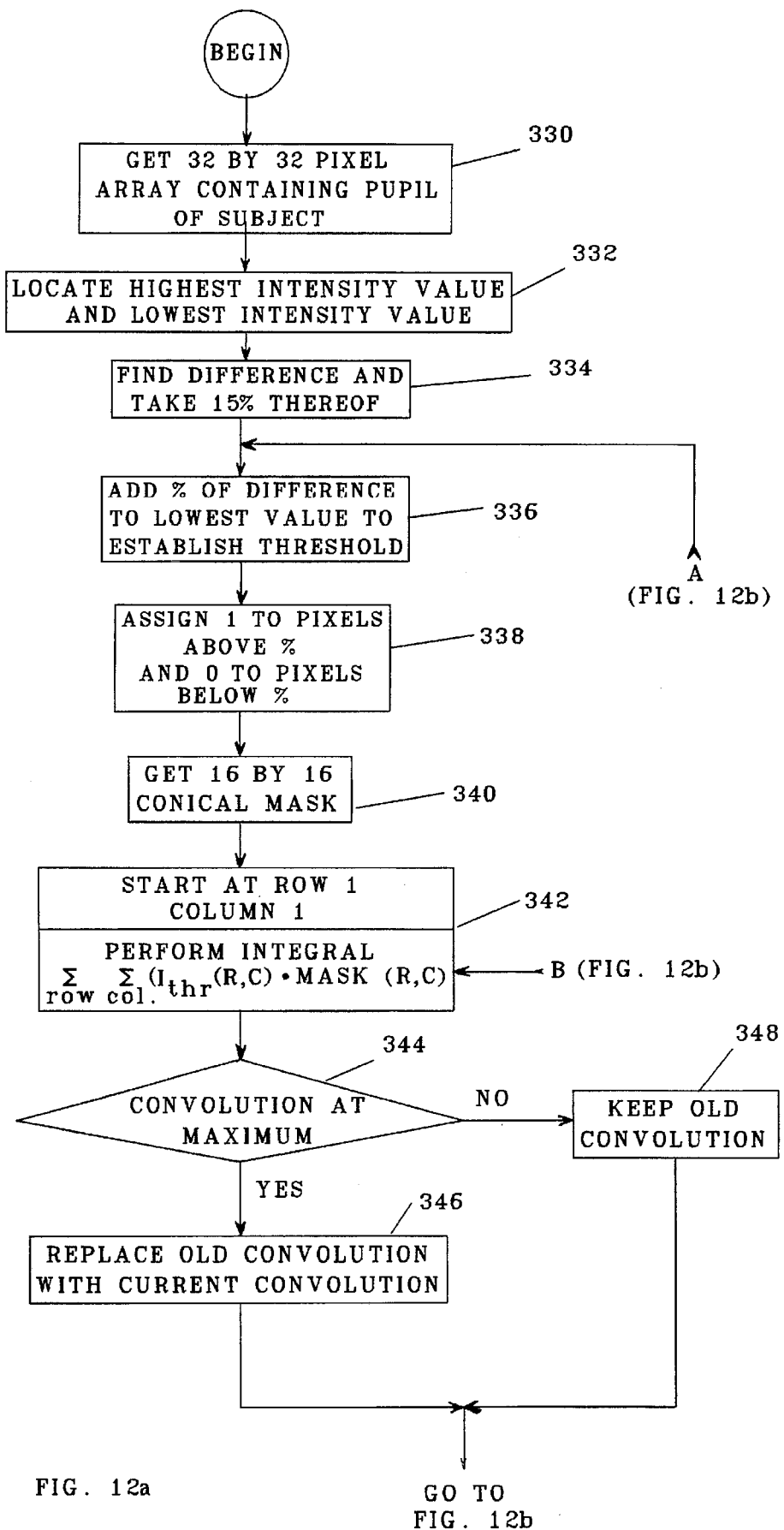
FIG. 12a is a flowchart of a method for locating a center axis of pupils of the eyes.
Figure 12B:
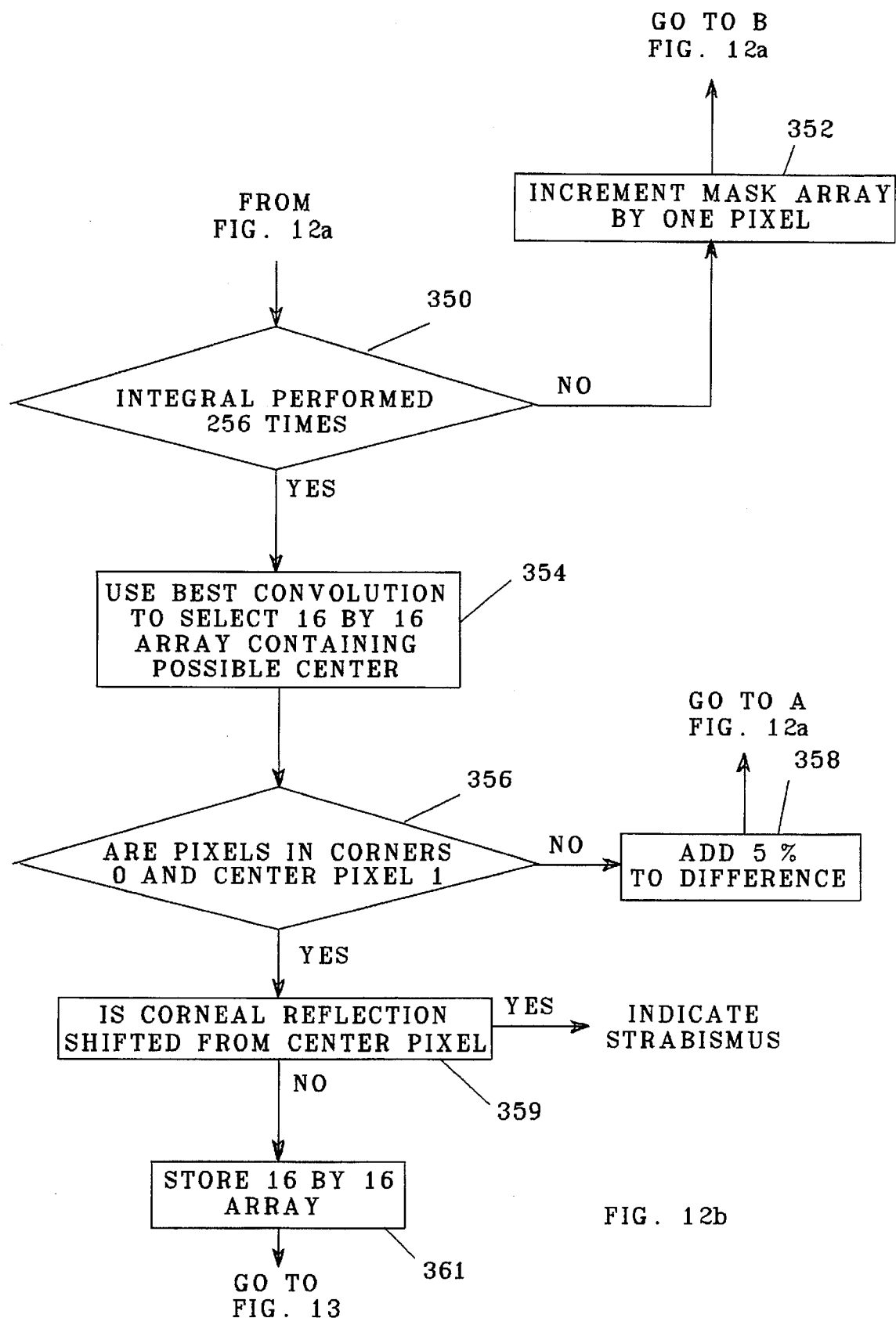

Next, as indicated by the flowchart of FIGS. 12a and 12b, the exact center of the eye is located based on circularity of the pupil and the distinct, sharp edge between the pupil and the iris. This process is facilitated by the fact that light reflected or scattered within the eye and emerging from the pupillary opening is always brighter than light reflected from the iris, which surrounds the pupillary opening. As such, intensity of light reflected from the iris is used as a baseline intensity for detecting light from the pupillary opening, allowing an exact center thereof to be precisely located.

In the prior described procedure for locating the eye data as shown in the flowchart of FIG. 10, an approximate center of the eye was located either by manually positioning a 32 by 32 pixel array over the pupil, or by a correlation function, which approximately centers the eye in a 32 by 32 array using a 16 by 16 mask of normal pupil data. This process is relatively inaccurate where a degree of strabismus is present in the subjects eyes, which causes the corneal reflection to appear shifted from a central location of the pupillary opening. In the process of the flowchart of FIGS. 12a and 12b, the exact center of the eye is located based on the presumption that the pupil is circular in shape and has a sharply defined dark edge between the iris and pupil. Where the pupil is not circular, as where the eye has been injured by accident, disease or a congenital defect, then the process of the flowchart of FIGS. 12a and 12b will locate the center of the pupil using a "best fit" algorithm.

Initially as shown at box 330 of FIG. 12a, a data cut of the 32 by 32 pixel array containing the pupil of the subjects eye located by using the corneal reflection as described in the flowchart of FIG. 10 is first performed. The 32 by 32 pixel array is used to assure that the pupil is within the array where strabismus is present. This 32 by 32 array is retrieved from memory, and scanned to locate the highest intensity value and the lowest intensity value of discrete pixels, as shown at box 332. In the following box 334, a difference value is found between the highest and lowest intensity values, and 15% of this difference is calculated. The program then falls through to box 336, where the 15% of the difference is added to the lowest intensity value to establish a threshold intensity level or value which is initially below an intensity value of pixels registering the iris. At box 338, a value of 1 is assigned to pixels in the 32 by 32 array having a value above the intensity threshold, and a value of 0 is assigned to pixels in the array having an intensity below the intensity threshold. As shown in FIG. 12c, which shows a light intensity graph through the center of a normal subjects pupil, light reflected from the iris is at an intensity I, with light emitted from the pupil being at a slightly higher intensity P. The intensity of the corneal reflection is manifested as a spike C. Significantly, Applicants have found that edges of the iris either absorb light, or scatter it in directions so that it is not received by the camera, which generates a dip E of intensity at the periphery of the pupil, which may serve as a distinguishing characteristic to detect edges of the pupil. Further, it has been observed that this edge of the iris is almost always circular, which is also used as a distinguishing characteristic of the pupil. As such, through a number of iterations by the process described above, a threshold T will be developed which is slightly above the level of reflected light I from the iris and below light P from the pupil, and which intersects the circular, rising edge E of the darker periphery of the pupil. By establishing the threshold slightly above the intensity of the reflection from the iris at the circular edge thereof and simply assigning a 1 to anything above the threshold, abnormal conditions of the eye which reflect light, such as refractive errors and opacities of the transparent media, are prevented from affecting the identification of a center point of the pupil.

After the data is thresholded as described, and as shown at box 340, a 16 by 16 pixel conical mask, which is incorporated and stored with the program in memory, is applied to the 32 by 32 pixel array from the subject to locate the center of the pupil. This mask is configured as shown in FIG. 12e, and has a center pixel C having an intensity value of 8, as contrasted to the thresholded intensity values of 0 and 1 in the subject eye array. Pixels in approximately concentric circles around center pixel C have intensity values which decrease with distance from center pixel C, as shown by intensity values of those pixels horizontally aligned with center pixel C, and the concentric arcs indicative of pixels having like intensity values at these radii. Pixels outside the 16 by 16 array may be assigned negative numbers which increase with distance from the 16 by 16 array. The center pixel C is designated as being the pixel intercepted by a line between the apex of the cone and the center of the circle at the base of the cone, this pixel being at row 8 column 8 of the 16 by 16 pixel array containing the conical mask. Thus, when the conical mask is located at different positions in the 32 by 32 pixel array containing the pupil of the subject, identification of location of the conical mask within the 32 by 32 array is facilitated by simply referencing the pixel in the 32 by 32 array which is in aligned relation with the center pixel of the 16 by 16 pixel array. Constructed as described, the conical mask has a shape optimized for locating a center of the eye irrespective of whether or not a diluent has been introduced into eyes of a subject, or where a subjects pupil is not perfectly circular.

While a conical mask is particularly described wherein sides thereof have a constant slope, it should be apparent that other configurations of masks, such as a cone having sides that vary exponentially, may be used to identify the center of the pupil. Additionally, edge detector algorithms for detecting the periphery of the subjects pupil may be used, with the number of pixels defining one or more radii of the pupil serving to locate a center pixel. As an example, a standard LaPlace filter or LaPlace edge detector, or the like, may be used to perform this function.

At box 342, the 16 by 16 array containing the conical mask is positioned in one quadrant of the 32 by 32 array, typically beginning at pixel row 1, column 1, and an integral performed between pixels of the mask and corresponding pixels of the 32 by 32 array. Here, the integral, as shown in the lower portion of box 342, is the double summation of the rows and columns of the thresholded intensity data times the mask row and column intensity data. This integral measures the degree of correlation between pixels of the 16 by 16 pixel conical mask and the respective pixels of the eye data, and indicates a maximum integral of convolution when the shape of the pupil is circular and centered exactly at a point on the cone.

By using this technique, allowance is made for error in the circularity of the pupil by allowing the cone shaped filter to generally center itself on a best fit basis within the pupil of the subject. This allows for cases where the pupil is not exactly circular.

After the correlation is performed, the program falls through to box 344, where the inquiry is made as to whether the convolution is at a maximum. If so, then the program proceeds to box 346, where a prior, lower value correlation previously stored in memory after a previous data convolution is replaced with the current higher correlation value. If the correlation value is lower than the previously stored correlation, then as indicated at box 348, the previously stored correlation value is retained in memory. After one of these steps is taken, the program proceeds to box 350 (FIG. 12b) where the inquiry is made as to whether the integral has been performed 256 times, the number of iterations necessary to step the 16 by 16 pixel conical mask through all possible positions of the 32 by 32 array taken from the subject. If all possible locations in the 32 by 32 array have not been examined, then the program goes to box 352, where the array containing the conical mask is moved by one pixel to the next position within the 32 by 32 pixel array. The program then loops back to the PERFORM INTEGRAL portion of box 342, and a new integral performed. If, at box 350, the integral has been performed 256 times, then the program falls through to box 354, where the convolution remaining in memory indicates a 16 by 16 pixel array in the 32 by 32 pixel array which probably contains the subjects pupil. Here, with the cone shaped mask superimposed over this 16 by 16 array of the subjects probable pupil, the axis of the cone, which extends between a center of the circle at the base of the cone and the apex of the cone, is taken to correspond with the center of the pupil and the optical axis of the subjects eye. This axis will extend through a single pixel of the 16 by 16 pixel array containing the subjects pupil, this single pixel being designated as the center of the pupil. At this point, the program proceeds to box 356, where the inquiry is made whether pixels in corners of the 16 by 16 array containing the subjects pupil have a value of 0, and as a further check, whether the pixel identified as being at the center of the pupil has a value of 1. If these conditions are not met, then the program proceeds to box 358, where 5% is added to the difference from box 336 (FIG. 12a) to develop a slightly higher threshold T (FIG. 12c), and the program loops back to box 336 to repeat the process as described. If, at box 356, the corner pixels are 0 and the center is 1, then the program proceeds to box 359, where an indication of strabismus may be provided. Notably, where pupils of a subject are dilated, as by introduction of a diluent, the pupil size may extend across sides of the 16 by 16 array. In this case, while the typical pupil expands only to about 18 pixels, there is an inherent allowance in the 16 by 16 pixel array for a pupillary size of up to 22 pixels across by virtue of the diagonal distance between corners of the 16 by 16 array.

With a knowledge of where the center point of the pupil is located, as obtained as described in the foregoing, the degree of divergence of the corneal reflection from the center pixel may be used to indicate a diagnosis of strabismus, with degree of divergence between the corneal reflection and the center pixel indicating severity of strabismus. Thus, a preverbal child may be quickly and easily diagnosed as being afflicted by strabismus, which may result in amblyopia, and the deviating eye identified by observing the shift of the corneal reflection with respect to the center of the pupil. At this point, at box 359, the inquiry may be made as to whether the corneal reflection is shifted from the center pixel of the 16 by 16 array containing the conical mask, and if so, an indication of strabismus made. Where this indication is made, the program may stop at this point, or proceed to the flowchart of FIG. 13 after storing the 16 by 16 array at box 361.

It should be evident that while a linear fit type of algorithm is disclosed above, a number of other algorithms may be used to identify the pupil using either the circular edge or the light emitted through the pupillary aperture, as where a contour of the rising edge E (FIG. 12c) may be matched using a mask including a normal rising edge in conjunction with a larger focal plane array having a higher resolution. Significantly, the notable feature here that facilitates accurate location of the pupil is detection of a sharp change in intensity of light at the edge of the pupil.

Figure 13A:
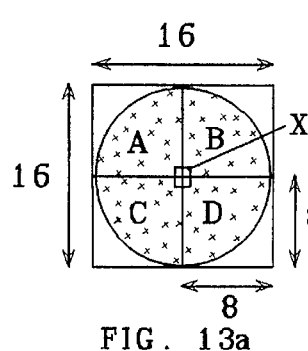
FIG. 13a–13d are views of a subject pupil showing intensities of light at various locations therein.
Figure 13B:
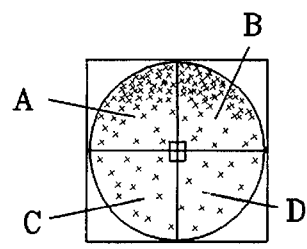
Figure 13C:
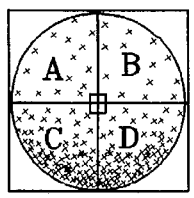
Figure 13D:
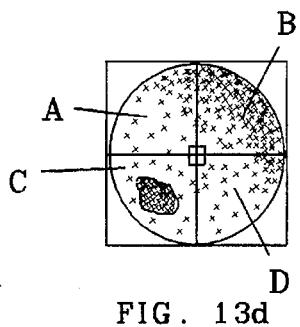
Figure 13:
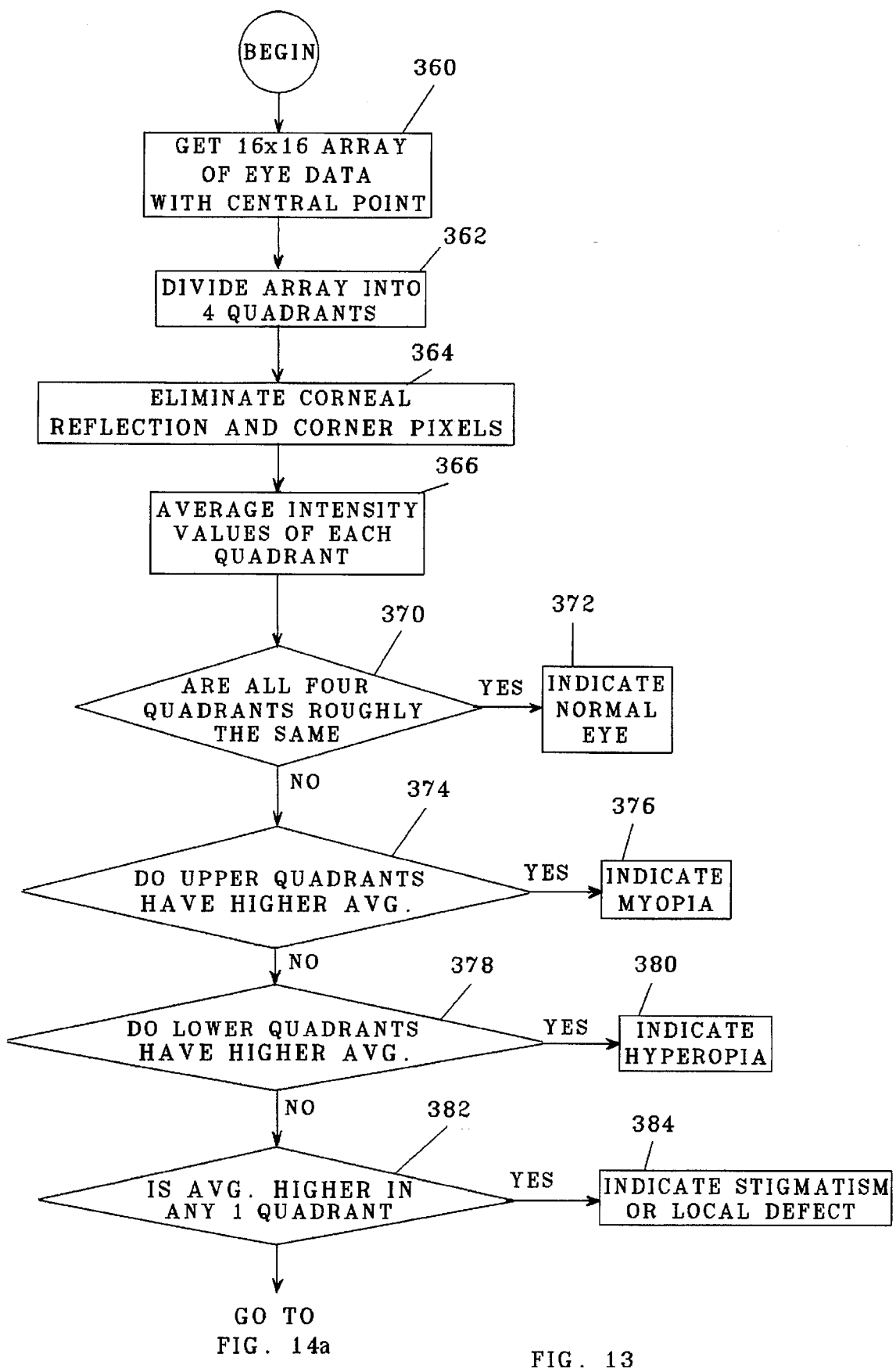
FIG. 13 is a flowchart of a method for providing analytical information to the user.

Next in the eye analysis program, and referring to the flowchart of FIG. 13, an analysis for diagnosing errors of refraction and local defects of the transparent media of the eye is undertaken. To implement this process, and as shown at box 360, the 16 by 16 pixel array containing the pupil of the subjects eye which was located as described in the flowchart of FIGS. 12a and 12b is retrieved from memory. This array is then divided into four equal quadrants A, B, C, and D, of 8 by 8 pixels each and as shown in FIG. 13a, as indicated at block 362. The program then falls through to block 364, where the corneal reflection, which typically falls within a 3 by 3 pixel area at the intersection of the four quadrants, is eliminated from further consideration (X in FIG. 13a) so as not to skew the averaging process of the following block 366. Additionally, the corner pixels are eliminated from consideration, so that the brightest and darkest intensity values are excluded so as to not skew the averages, leaving 28 pixels in each quadrant. In this averaging process, which includes taking a standard deviation of each quadrant, the pixel intensity values of the 28 pixels in each of the four quadrants A, B, C, and D are discretely averaged to obtain an average intensity value for each quadrant. As described in the foregoing, a normal eye is uniformly illuminated, while a nearsighted eye produces a brighter reflection in the two upper quadrants, and a farsighted eye produces a brighter reflection in the two lower quadrants. Thus, as indicated at block 370, if substantially the same faint, average illumination is registered by pixels of all four quadrants, which generates approximately the same average value, then the program indicates a normal eye at block 372. Where the standard deviation of the four quadrants is not substantially the same, then the program falls through to box 374. Here, the inquiry is made as to whether the upper quadrants A and B have a higher average value than the lower quadrants C and D, as where the characteristic bright crescent shaped reflection of myopia is present in upper quadrants A and B (FIG. 13b). If this is the case, then myopia is indicated at box 376. If the upper quadrants A and B do not have the higher average, then the program falls through to box 378. Here, the inquiry is made as to whether the lower quadrants C and D have the higher average, as when the characteristic bright crescent reflection indicative of hyperopia is present in the lower quadrants C and D, as shown in FIG. 13c. If so, then hyperopia is indicated at box 380. If this is not the case, then the program proceeds to box 382, where the inquiry is made as to whether any single quadrant of quadrants A, B, C, and D has a higher average than the others. In this instance, one quadrant may contain the majority of the characteristic crescent reflection of stigmatism in conjunction with myopia or hyperopia, as shown in quadrant B of FIG. 13d, or a local defect, such as a cataract, as shown in quadrant C of FIG. 13d. Where an indication of strabismus is not provided as described above by the conical mask, ocular misalignment at this point causes the corneal reflection to be shifted into one quadrant, skewing the average of that quadrant and causing an indication of refractive error, which is analyzed as will be further explained.

Figure 14A:
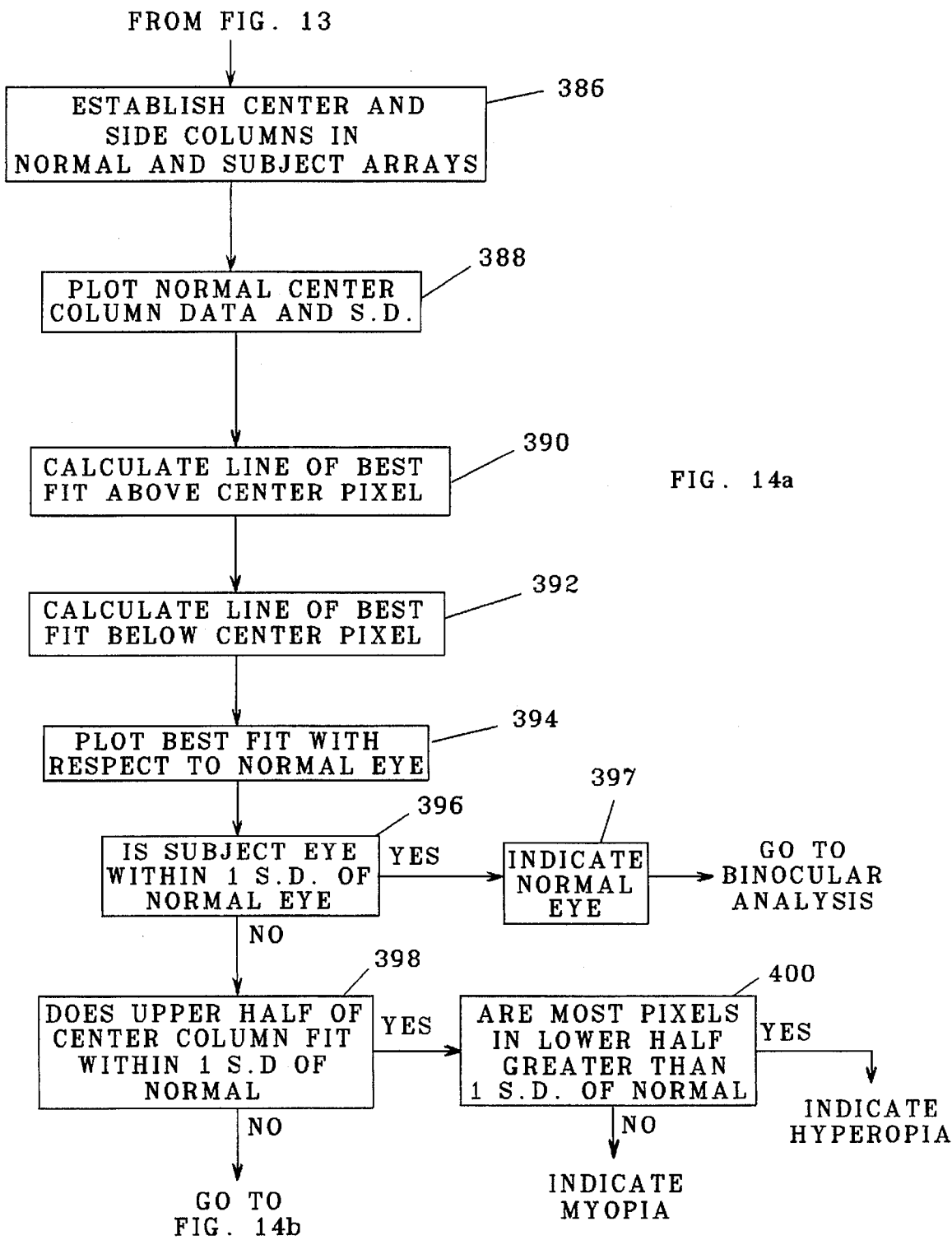
FIG. 14a is a flowchart of a method of analyzing pupils of a subject.
Figure 14B:
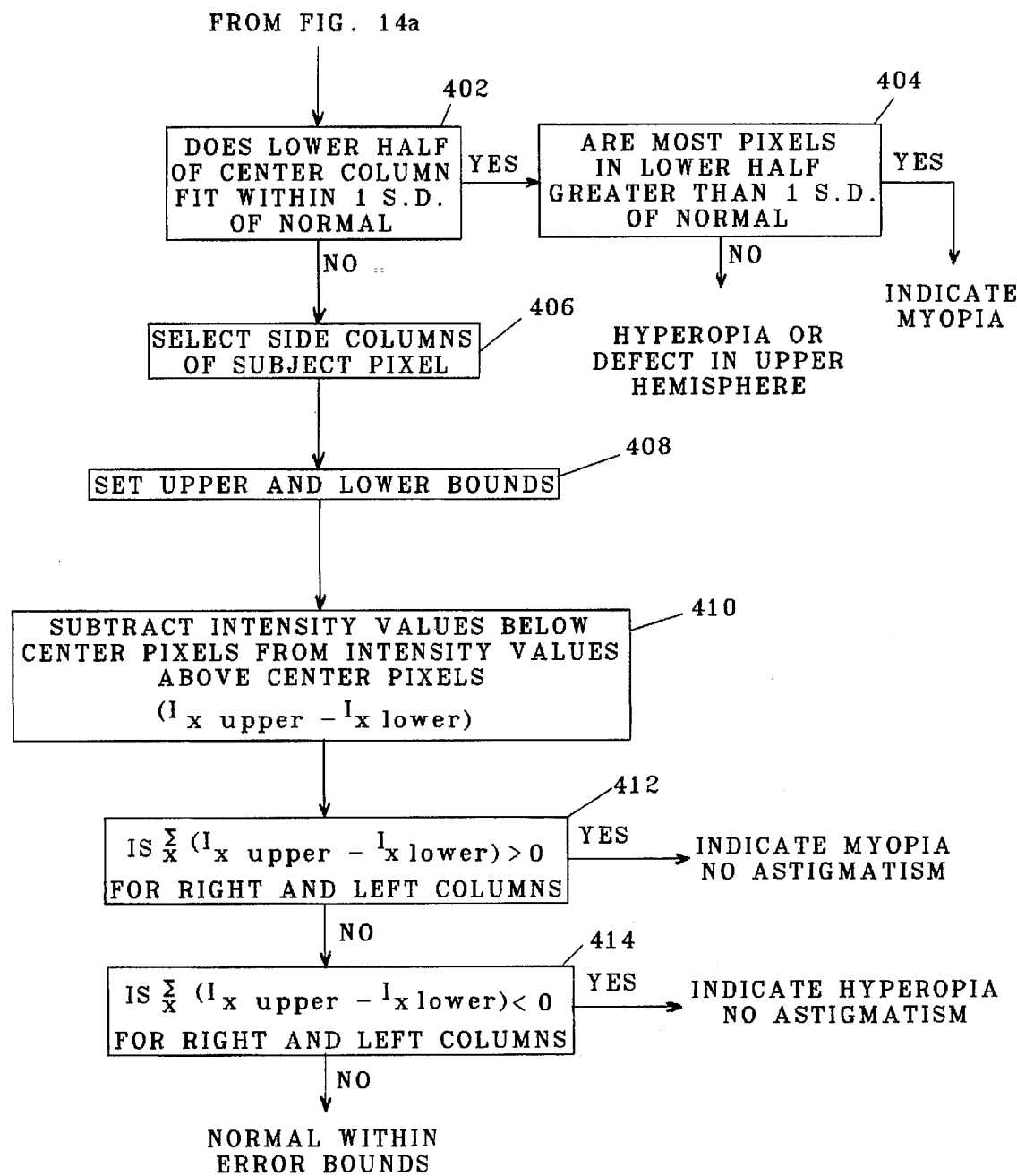
Figure 14C:
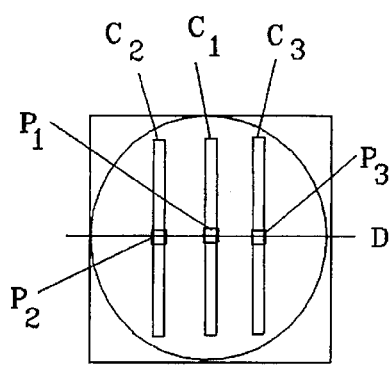
FIGS. 14c–14g are illustrations relating to a method of analysis of the present invention.

The program next proceeds to the flowchart of FIG. 14a, where, and as shown at box 386 and in FIG. 14c, the 16 by 16 normal eye array used as described above for the optional process for locating the pupil and the 16 by 16 pixel array of the subject pupil are retrieved from memory, and columns of pixels $C_1$, $C_2$, and $C_3$ one pixel wide selected for further analysis. The center column $C_1$ is aligned with the center pixel $P_1$ at row 8, column 8, pixel $P_1$ being horizontally aligned with center pixels $P_2$ and $P_3$ in side columns $C_2$ and $C_3$, respectively, dividing the image of the pupil horizontally into upper and lower hemispheres as shown by line D. Side columns $C_2$ and $C_3$ are each spaced 3 pixels from column $C_1$, with ends of all the columns terminating at points within the pupil so that mathamatical analysis of intensity values of points within these columns is confined to intensity values of the pupil. Additionally, the number of pixels above and below the center pixels are the same, so that intensity values of respectively positioned pixels above and below the center pixels are directly comparable, which gives a more sensitive indication of refractive error than the global measurements as described in the foregoing.

Figure 14D:
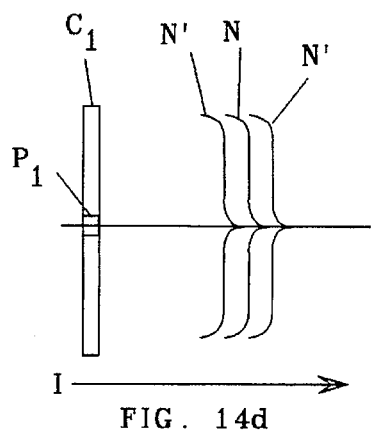

As shown in FIG. 14d and box 388, the intensity plot of the center column of pixels of a normal pupil N is shown, with the line indicated by $P_1$ referencing the center pixel at row 8 and column 8. As such, intensity values above line $P_1$ represent intensity values of discrete pixels above the center pixel, and intensity values below line $P_1$ represent intensity values of discrete pixels below the center pixel, with intensity values increasing with distance to the right. An envelope of standard deviation may be calculated and positioned on either side of plot N, as indicated by dashed lines N', with the distance between N and either of lines N' representative of a selected standard deviation, such as 1, which corresponds to a refractive error of about 1.25 diopters.

Figure 14E:
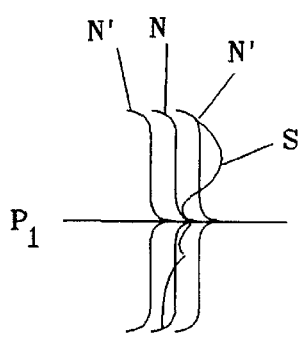

The pixels of the center column of the subject pupil are plotted in superimposed relation with respect to the plot of FIG. 14d, and at boxes 390 and 392 portions of this plot above and below the center pixel $P_1$ are compared with respective portions of the normal plot N. A line of best fit of intensity values above and below the center pixel of the subject pupil with respect to corresponding intensity values of the normal pupil is found by calculating a constant which when added or subtracted to/from the normal pupil intensity values results in the closest match to the normal pupil array, as by finding the difference between discrete subject intensity values and corresponding normal intensity values, squaring the difference, and summing over all pixels. The best fit occurs when this sum is minimized. This process preserves the shape of the subject pupil curve, and shifts it so that the shape of the subject pupil curve is matched as closely as possible to the normal pupil curve. At box 394, the subject pupil data is plotted superimposed with the normal pupil data and displayed for visual examination by the user. In this manner, a vertical center region of upper and lower hemispheres of the subject pupil is compared with a corresponding vertical center region of the upper and lower hemispheres of the normal pupil, with the plotted intensities of the subject pupil having a closest match to the plotted intensities of the normal pupil being aligned. As such, where greater intensities are registered by pixels above the center pixel of the array containing the subject pupil, as in the case of myopia, then the plot may appear similar to that shown in FIG. 14e, where the plot of the subject pupil is designated S. Here, the plot of the upper portion of S above pixel $P_1$ registers the bright crescent indicative of myopia, and extends beyond envelope N' indicating a degree of myopia in excess of 1 standard deviation of normal, with this being shown graphically as in FIG. 14e, or by one of any number of methods as is known to those skilled in the art. Where pixels in the center column below the center pixel in the subject pupil register higher intensities of the bright crescent, as where hyperopia is present, then the plot appears approximately as shown in FIG. 14f. Where the plot of the central column of the subject pupil falls within the envelope defined by dotted lines N', the eye is deemed to be without significant refractive error.

Figure 14G:
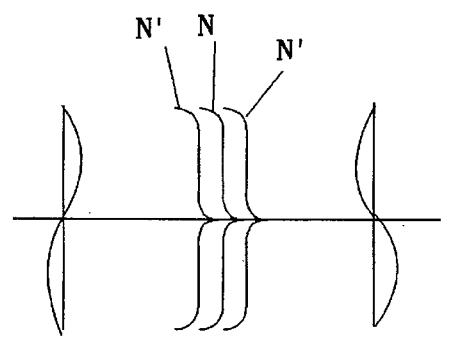
Figure 14F:
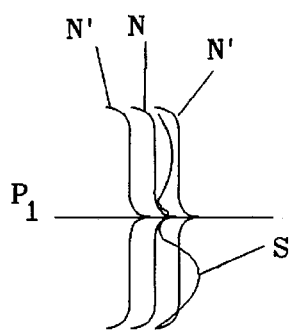

In FIG. 14g, a plot is shown where data from the two side columns is superimposed, with the plot from each column being of a different color. Here, where oblique astigmatism is present in the subject, pixels of the column registering the greater intensity light from the quadrant of the pupil reflecting the bright crescent indicative of astigmatism will generate a line which deviates from a line generated by pixels of the column registering less light.

By performing the shifting process and subsequent best fit of the shape of the curve, the effects of minor aberrations are minimized and better determinations of refractive errors are made. For example, a myopic eye may also have a defect, such as a cataract, which tends to decrease the light intensity in the upper hemisphere and hence cause it to initially appear normal. However, the lower hemisphere intensities will still be less than the upper hemisphere intensities, and the proper diagnosis of myopia will be indicated.

At box 396, the inquiry is made as to whether the curve of the subject pupil as described above is within the envelope of 1 standard deviation, and if so, then an indication of a normal eye is made, and operation of the program proceeds to an analysis of the binocular state of the eyes. Where the upper or lower portion of the curve cannot be fitted within the envelope, then the program proceeds to box 398, where the inquiry is made as to whether the upper half of the curve fits within the envelope. If so, then the inquiry is made at box 400 as to whether most pixels in the lower portion of the curve are greater than the normal average plus 1 standard deviation, and if so, then hyperopia is indicated. If the answer to this inquiry is no, meaning that the majority of pixels in the lower hemisphere are less than the normal average minus 1 standard deviation, myopia or a defect in the lower hemisphere of the subject's pupil is indicated.

In FIG. 14b, the program proceeds to box 402, where the inquiry is made with respect to whether the lower half of the center column fits within 1 standard deviation of normal. If the answer is yes, then the inquiry is made at box 404 as to whether most pixels in the lower half are greater than 1 standard deviation of normal. If the answer is yes, then myopia is indicated. Where the answer is no, myopia or a defect in the upper hemisphere of the pupil is indicated. Where the lower half does not fit within one standard deviation of normal, then the program falls through to box 406, where the side columns C2 and C3 (FIG. 14c) of the subject pupil are examined in order to compare respective side regions of the upper and lower hemispheres of the subject pupil. This further analysis is required because neither the upper or lower hemispheres fit within one standard deviation of normal data, as indicated by the NO responses at boxes 398 and 402. At the following box 408, a number is entered which sets upper and lower bounds with respect to further detection of myopia and hyperopia, with practical limits being from zero, a greatest sensitivity of detection to about 20, which is the least sensitive practical limit.

At box 410, intensity values of pixels in side columns $C_2$ and $C_3$ below center pixels $P_2$ and $P_3$ are subtracted from intensity values of respectively positioned pixels above center pixels $P_2$ and $P_3$. The program falls through to box 412, where the inquiry is made as to whether the summation of these differences is greater than zero for the right and left columns, and if so, then myopia with no astigmatism is indicated. If the difference is less than zero, then the inquiry is made at box 414 as to whether the summation is less than zero. If the answer is yes, then hyperopia with no stigmatism is indicated. If the answer is no, meaning that while slight refractive error may be present, the pupillary response is within the error bounds set in box 408.

By the process shown in boxes 408–412, and with the bounds set to zero as shown and described, the smallest degree of myopia, hyperopia, stigmatism, or a transparent media opacity will be detected. Where it is desired that subjects having a relatively small degree of refractive error, and which suffer no significant reduction of visual acuity therefrom, be classified as having normal vision, then the zero bounds may be increased to a specified number by the user. For example, where the zero value is replaced by 6, which corresponds to one standard deviation and a refractive error of about 1.5 diopters, then only where the summation of the differences in boxes 410 and 412 is greater or less than 6, or 1 standard deviation, respectively, would indications of myopia or hyperopia be indicated. Where a value of 2 is selected, any myopia or hyperopia in a subject which is greater than about 0.5 diopters would generate an indication of myopia or hyperopia.

Imperfections in the lens and ocular media in a subjects eyes causes the retinal reflex light to be distorted as described above, resulting in non-uniform intensity across the reflex. The algorithms described hereinafter are designed to detect such non-uniformity and measure extent thereof, which is indicative of severity of refractive error of the lens and ocular media.

Distortion of the light impinging on the CCD array caused by imperfections in the ocular media is manifested as rapid spatial variation of intensity of the light such that adjacent pixels can have widely varying intensity values, whereas for the normal eye, variations are small. The variance in the average intensity of light in a quadrant of the pupil is used to determine relative magnitude of the distortion. Where distortion is greater, a higher variance is produced in the quadrant averages. The variance is calculated by averaging the intensity values for 28 pixels receiving the retinal reflection within a given quadrant and calculating the standard deviation of that average using statistical analyses. A high standard deviation is indicated by values of 6 or more, and indicates a non-normal eye condition.

Figure 15:
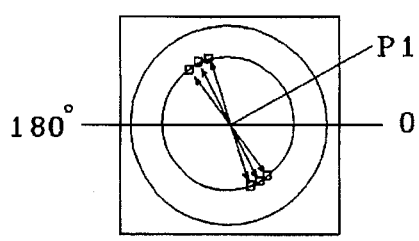
FIG. 15 is an illustration including radially opposed pixels which are selected for light intensity analysis.

Distortions in focusing power of a lens is determined by comparing intensity values of radially opposed pixels with respect to the pupillary axis, as shown in FIG. 15. The logarithm of the ratio of the intensities of two radially opposed pixels is then a measure of the optical distortion of the lens. The ratio so defined is plotted for a plurality of pairs of radially opposed pixels at a selected radius from the pupillary axis, and each selected radius is plotted with a unique color so as to distinguish between different radii when viewing the resulting plot. The plot is such that the intensity ratio is plotted along the vertical axis, and angular position of the pixels is plotted along the horizontal axis. In this manner, small defects in the optical media of the subject become apparent as successively greater radii are examined.

Figure 15A:
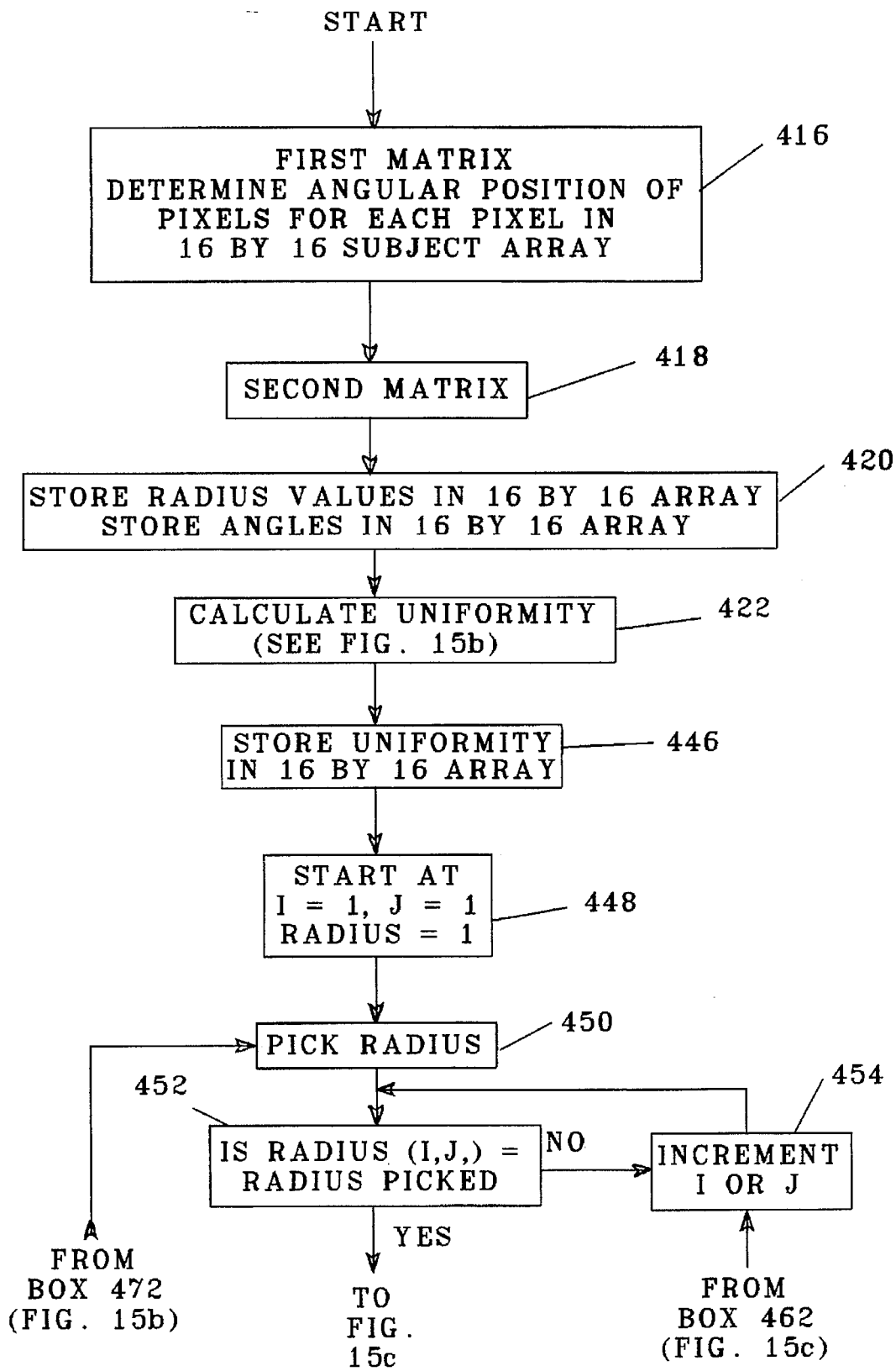
FIG. 15a is a flowchart showing mathamatical analysis of intensity of a subject pupil.

Referring now to FIG. 15 and the flowchart of FIG. 15a, the process for determining distortions in focussing power of a lens is shown. Here, two 16×16 matrices are formed by the operations of blocks 416 and 418, with the matrix formed by block 416 receiving values of angles that a line drawn between the center pixel $P_1$ of the 16 by 16 pupillary array of the subject, which is obtained as described in the foregoing, and the pixel of interest makes with a horizontal line drawn through the center of the pupil. The matrix formed at block 418 receives the radial distance of each pixel from the center pixel $P_1$. The position of each element in these two matrices corresponds to position of a pixel in the subject pupil array at the same row and column number. The radius or distance from the center pixel to a particular pixel is calculated using the following formula:

$$\text{ANGLE} = \text{ARCSIN}\left(\frac{\text{COLUMNS} - 8}{\text{RADIUS}}\right)$$

The corresponding angle is calculated using:

$$\text{RADIUS} = \sqrt{(\text{COL.} - 8)^2 + (\text{ROW} - 8)^2}$$

Specifically, the starting row and column number are both initialized to 1 and the radius and angle are calculated, and stored in the matrices as indicated at box 420. The row number is incremented by 1, and the calculation is repeated and the results stored at sequential row positions in the respective matrices until all 16 rows have been analyzed. The process is repeated incrementing the column numbers in the same way until the calculations have been completed for all 256 elements of the angle and radius arrays, as indicated at block 420.

Figure 15B:
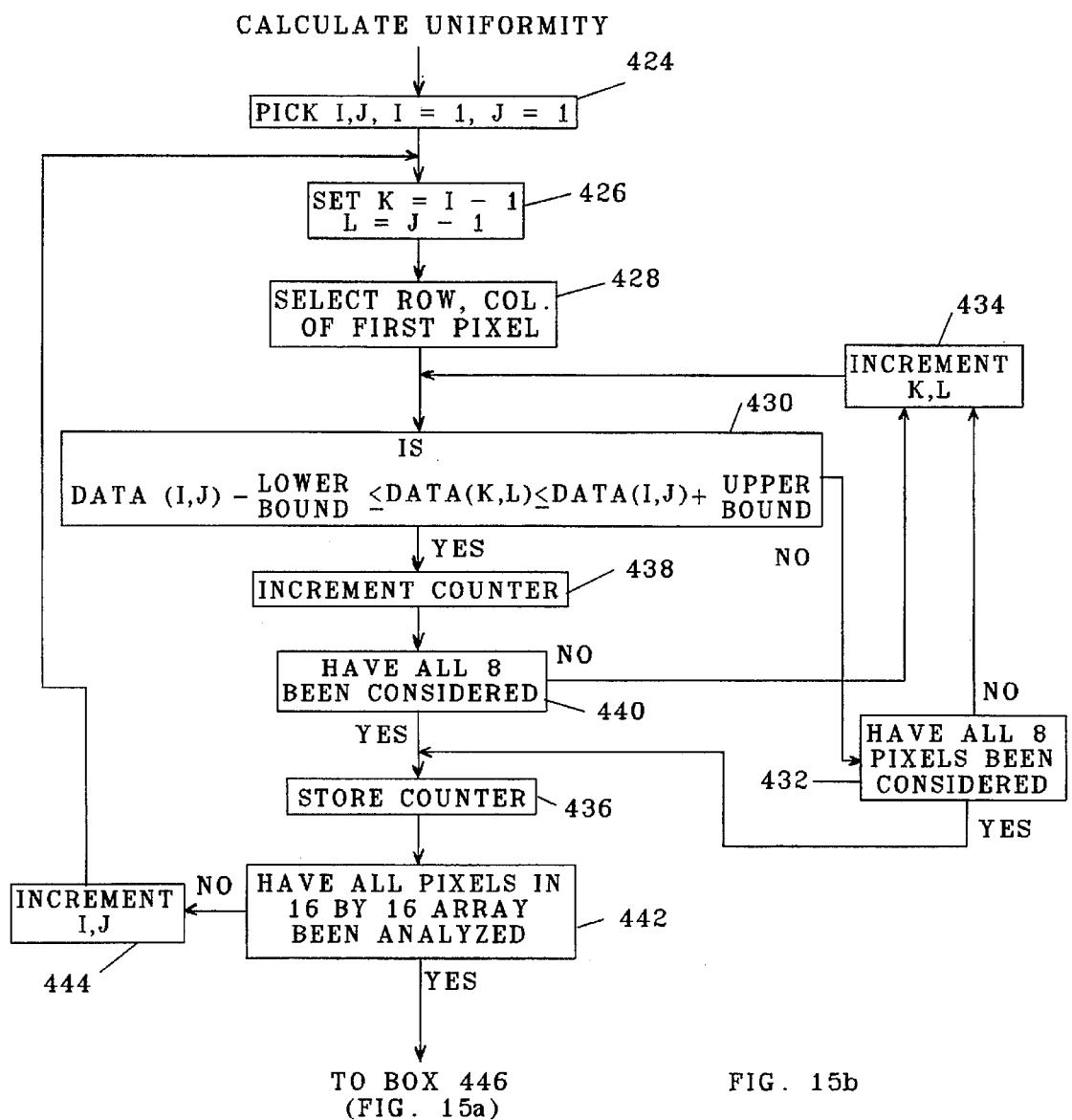
Figure 15C:
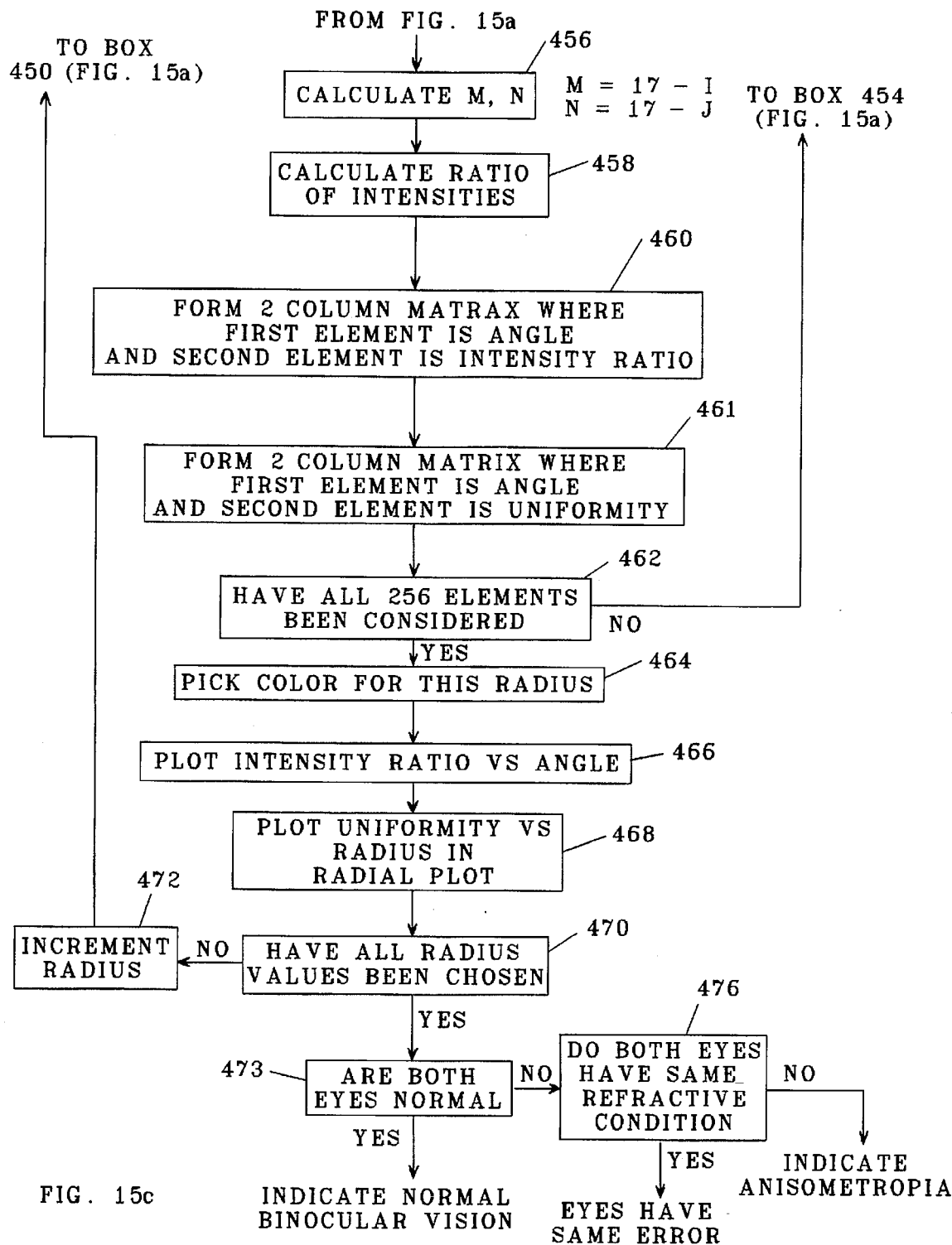

Next, uniformity of intensity of light from the pupil is calculated as shown at box 422 and in the flowchart of FIG. 15b. This uniformity is defined as the number of adjacent pixels surrounding the pixel being evaluated that have nearly the same intensity value. In general, for normal eye data, all 8 pixels surrounding the pixel being evaluated, excluding the central pixels comprising the corneal reflection as described above, have the same intensity values, as contrasted to subjects with cataracts or other severe distortions of the optical media, these distortions causing intensity values of the adjacent pixels to vary greatly. The number of pixels with the same intensity values within selected limits chosen by the user is counted using a variable for counting and stored in memory, with the selected limits defining resolution of uniformity.

Figure 16:
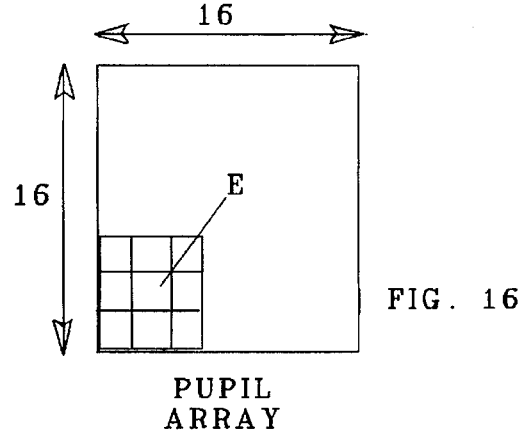
FIG. 16 is an array of a pupil of a subject showing a second array positioned therein which is used for intensity analysis.

Initially, the row and the column number of a new 16 by 16 uniformity array of the pupil is set to row 1 and column 1 as shown at block 424, where I is a row number and J is a column number. The upper and lower intensity bounds are set at block 426 to default values from a setup file or by values selected by the user. The upper limit is set at the intensity value of the pixel being evaluated plus the upper bound whereas the lower limit is the intensity value minus the lower bound. As an example, the intensity value might be 40 with an upper bound of +2 and a lower bound of −2. The range of acceptable uniformity is then 38 (40 minus 2) to 42 (40 plus 2). At box 428 the row and column number of the first pixel designated 1 (FIG. 16) of 8 pixels adjacent a center pixel E is selected. Initially, pixel 1 at row 1 column 1 is first tested for uniformity, then the pixel at row 2 column 1, and so forth. While this particular pattern is disclosed, any pattern of discretely selecting pixels adjacent pixel E for analysis may be used. The intensity of each pixel adjacent the pixel being evaluated is compared at box 430 to see if it is within the range defined at block 426, and if so, then the counter variable is incremented. Specifically, a test is made to determine whether the adjacent pixel is simultaneously greater than or equal to center pixel E in FIG. 16. In the instance where the answer to this inquiry is NO, then the inquiry is made at box 432 as to whether all eight pixels around pixel E have been considered. If the answer is NO, the program proceeds to box 434, where either K or L is incremented, selecting the next pixel for evaluation. If, at box 432, all eight pixels have been evaluated, then the answer is YES, and the program proceeds to box 436 and the counter value is stored, indicating all eight pixels around pixel E have been evaluated. Where the answer to the inquiry at box 430 is yes, then counter 438 is incremented, indicating that a uniform pixel is added to the count. At box 440, the inquiry is made as to whether all eight pixels surrounding pixel E have been examined. If the answer is NO, then the program proceeds to box 434 where the next pixel adjacent to pixel E is selected. The examination is again made at box 430. If all eight adjacent pixels have been selected at box 440, then the program proceeds to box 436, where the number of uniform pixels is stored. The program then proceeds to box 442, where the inquiry is made as to whether all pixels in the 16 by 16 subject pupil array have been analyzed. If the answer to this inquiry is NO, then the program proceeds to box 444 where the next pixel in the subject pupil array is selected. The process then proceeds as described in the foregoing through boxes 428 to box 436. If the answer to the inquiry at box 442 is YES, and referring now to the flowchart of FIG. 15a, the program proceeds to box 446, where uniformity values of pixels in the 16 by 16 pixel array of the subject pupil are stored. The process is repeated until all eight of the adjacent pixels have been evaluated. In this way, the maximum uniformity value which can occur is 8, which would indicate that all 8 of the adjacent pixels have nearly the same intensity value. These uniformity values are in inverse relation to optical distortion of a subject's eye, so a value less than 8 indicates that optical distortion is present, with increasing distortion indicated by a lower uniformity value. This value of uniformity is then stored in a new 16×16 array at the same row and column number of the pixel in the subject array being evaluated. For example, referring back to FIG. 16, if the pixel at row 5, column 4 in the subject data is being evaluated, the program counts the number of pixels adjacent to the pixel at row 5, column 4 that have nearly the same intensity value. If six of the adjacent pixels had intensity values within the defined limits of the subject pixel, then a value of 6 would be stored in the uniformity array at row 5, column 4.

The next step in the process is to calculate the intensity ratio as described earlier. The process starts at block 448 (FIG. 15a) by setting the row number and the column number to 1. Next the radius is set to 1 at block 450. A test is made at block 452 to determine if the value stored at row 1 and column 1 in the radius matrix calculated in block 418 is equal to the radius under consideration. If not, the column number is incremented by 1 at block 454 and the process is repeated. If the result is yes, then the row and column number of the corresponding pixel opposite to the pixel being evaluated is calculated as at block 456. The pixel opposite the pixel being evaluated is defined as the pixel at the same radial distance from the center as the pixel being evaluated and on opposite sides of the central pixel (pupillary axis) as indicated by arrows designating opposite pixels in FIG. 15. For a 16×16 matrix the row (M) and column (N) positions of the opposite pixel is simply 17 minus the row number and 17 minus the column number respectively. For example, if the subject pixel location is at row 4, column 5, then the pixel directly opposite would be at row 13 (17 minus 4) and column 12 (17 minus 5). Next the intensity ratio shown at box 458 is calculated using the following formula:

$$\text{INTENSITY RATIO} = \text{LOG}_{10}\left(\frac{\text{SUBJECT PUPIL DATA AT ROW } I \text{ \& COL. } J}{\text{SUBJECT PUPIL DATA AT ROW } M \text{ \& COL. } N}\right)$$

Figure 17:
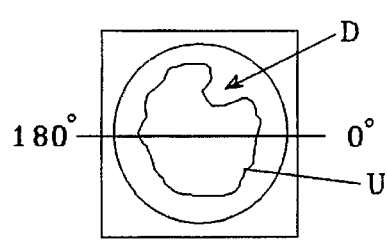
FIG. 17 is a radial plot of the present invention showing an ocular defect.

The resulting intensity ratio value is stored in a two dimensional matrix at box 460, the matrix having with two columns of numbers. The angle corresponding to the subject pixel location is stored in the first column and the intensity ratio defined above is stored in the second column. In addition, at box 461, another two column array is formed wherein the first column contains the angle corresponding to the subject pixel location and the second column corresponds to the uniformity stored at pixel location row I, column J as described at box 446. A test is made at block 462 to see if all 256 pixels in the subject array have been evaluated. If not, the program loops back to box 454 (FIG. 15a) where the row and/or column numbers are incremented and the process continues as previously described between boxes 452 and 462. This increases speed of the computational process and allows plotting of uniformity values at specific constant radii. Once all 256 values have been evaluated as indicated by a YES at box 462, a color is picked at box 464 to correspond to the radius chosen, and the results are plotted at box 466. Next at box 468, the uniformity results are plotted, with an example of such a plot shown in FIG. 17. Here, the circle represents a perfect uniformity value of 8, with proximity of line U with the circle indicative of uniformity of light from the subject pupil. The inner deflection D in the upper right quadrant represents an optical defect, such as a cataract, in a corresponding quadrant of the pupil of a subject. A test is made at box 470 to see if all desired radii have been considered. If not, the program increments the radius value at box 472 and the program loops back to box 450 (FIG. 15a) where the entire process is repeated from box 450 to box 470 until all radii have been evaluated. The user can optionally set the number of desired radii and the corresponding values in order to preclude unwanted analyses. The example program given in the appended source code limits the radii under consideration to values of 3, 4 and 5 units for convenience.

At box 473, the test is made as to whether both eyes are normal. If the answer is YES, normal binocular vision is indicated. If the answer is NO, then the program proceeds to box 476, where the test is made as to whether both eyes have the same refractive error. If the eyes have differing refractive powers, then anisometrophia is indicated. If the eyes have the same refractive power, as indicated by a YES, then the program is terminated.

While a particular embodiment is disclosed in the foregoing, and which is described in conjunction with a focal plane array of a particular size and type, it is apparent that other types of focal plane arrays may be used with the principles described herein, as will be apparent to those skilled in the art. This image enhancement may be the addition of artificial color wherein brighter portions of the reflection are depicted as white areas, with less intense graduations appearing as red, yellow, and green areas, respectively. Further, artificial topography may be applied to the images from the eyes to vertically plot the relative intensities of light issuing therefrom. In this instance, and in combination with the artificial color scheme, the brightest, white areas would extend to a highest level, with the white areas surrounded by lower red areas, in turn surrounded by lower yellow and green areas, respectively. Additionally, pattern recognition software may be employed to recognize signatures of normal eyes and the signatures of a number of commonly encountered problems of the eyes, such as nearsightedness, farsightedness, cataracts, etc.

In preparation for use, computer 78 is activated, and the operating system and software for camera 72, and any other software, are loaded into its internal memory. Annular light apparatus 34 is activated, which projects an image of the circularly travelling spot of light to mirror 18, which in turn reflects this image through opening 24 of baffle 22 to beamsplitter 16. Beamsplitter 16 reflects a portion of the image to head positioning station 28, dimming the lights from the light apparatus by about 40%. Flash 26 is activated and readied for the first flash. At this point, illumination of the room wherein the detection device is located is dimmed, so as to promote dilation of the subjects pupils and to make the fixation light more visible. The first subject places his/her chin in the chinrest, and the chinrest is adjusted as necessary to place eyes thereof in a plane of analysis. Typically, the chinrest need only be adjusted once for a particular age group of children or adults. The subject is instructed to look at the moving lights, which as seen projected on beamsplitter 16, are at a different focal distance and are relatively dim and indistinct. Movement of the lights causes eyes of the subject to attempt fixation thereon, but defocussing of the eyes is instead effected by the difference between the focal distances of the beamsplitter and the dim, moving light from light apparatus 34. Flash 26 is then energized to produce a flash, which produces beam 56 from telescopic lens system 60 and which is directed through annulus 70 of ring flash 35. Beam 56 impinges on mirror 18, which reflects the beam through opening 24 of baffle 22 to beamsplitter 16. Beamsplitter 16 reflects a portion 56b of the beam as described to eyes of the subject, generating the reflection from the retina and reflection from the cornea. The reflection from the retina and reflection from the cornea is reflected by beamsplitter 16 through opening 24 to mirror 18, which in turn reflects these eye reflections back toward telescopic lens system 60 and camera lens 74. With the angular separation between the light source and camera adjusted as described to about 1 degree, any portion of the retinal reflection refracted by an eye having a refractive error from about 0 diopter or greater in a positive direction or from about −1.75 diopters or greater in a negative direction is, in addition to the reflection from the cornea, recorded by camera 72 and digitized by control circuitry 76, with the digitized image provided to computer 78 and displayed on monitor 80. The region between about 0 diopters and −1.75 diopters is a null region produced by inversion of the retinal reflex by nearsighted eyes.

This is shown in FIG. 8a, 8b, and 8c, wherein an eye with no refractive error (FIG. 8a) focusses the retinal reflection R directly back to lens system 60 from where the beam of light emerges. Thus, none of the light of the retinal reflection is received by lens 74. A farsighted eye (FIG. 8b) produces divergence of retinal reflection R so that as the retinal reflection diverges, a portion of the reflection is received by camera lens 74 and appears at the lower quadrants of the pupillary opening of the eye. With edge 74a of lens 74 positioned at a point corresponding to about 0 diopter, any diverging retinal reflection from a farsighted eye is received by lens 74. Conversely, the nearsighted eye, (FIG. 8c) causes inversion of the retinal reflection R such that the reflection appears at the upper quadrants of the pupillary opening of the eye. As such, an inversion region 75 of the retinal reflection between about 0 and about −1.75 diopters wherein the retinal reflection is inverted is a null region not detectable by lens 74.

In the instance where it is desired to detect lessor or greater errors of refractive index of the eyes, the angular separation between beam 56 and the axis of camera lens 74 is decreased or increased, respectively, by vertically adjusting mount 58 or edge 68 as described. Additionally, null region 75 (FIG. 8c) may be shifted to about +0.5 diopters to about −1.0 diopters as shown by dashed line null region 75a by positioning a relatively weak lens 77 (dashed lines in FIGS. 7 and 8c) so that a subject looks through lens 77 at beamsplitter 16. This allows for greater sensitivity in detecting nearsightedness than otherwise would be possible.

Figure 3:
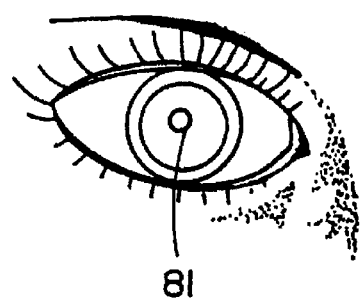
FIGS. 3–6 are illustrations of eyes of subjects recorded by the present invention and having certain disorders.
Figure 3:
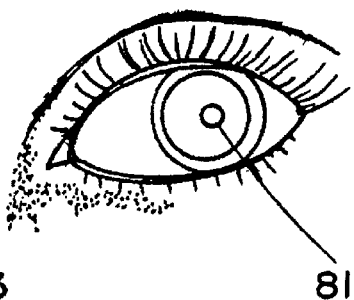

In this device, a variety of abnormal conditions may be quickly detected and displayed on monitor 80 in real time, or stored for later analysis. For instance, diagnosis of strabismus (FIG. 3) is made when the points of light 81 reflected by the cornea are not identically positioned in each eye. Here, the cornea of the deviating eye will reflect a point of light that is not centrally located in the pupillary opening or equidistant from sides of the eye. Refractive error defects of either myopia (nearsightedness) or hypermetropia (farsightedness) produces a reflection on one side of the cornea depending on the focal length of the eye and the position of the light source. In the instant invention, with the light source positioned below the camera lens, nearsightedness (FIG. 4) is indicated when bright portions of the retinal reflection are observed along upper sides of the opening of the pupil. The degree of severity of myopia is indicated by extent of the illuminated area of the pupil which is visible from the camera, with a larger area indicating a worse condition than a smaller, narrower area. Farsightedness (FIG. 5) is similarly indicated, except the illuminated area occurs along lower sides of the pupil, with degree of severity also indicated by extent of the illuminated area.

Figure 4:
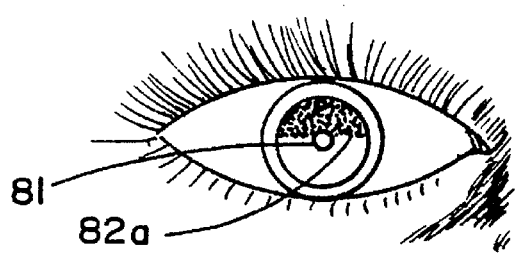
Figure 4:
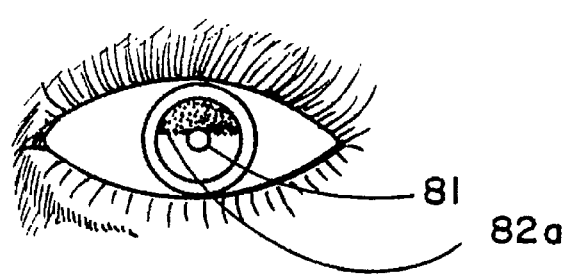
Figure 5:
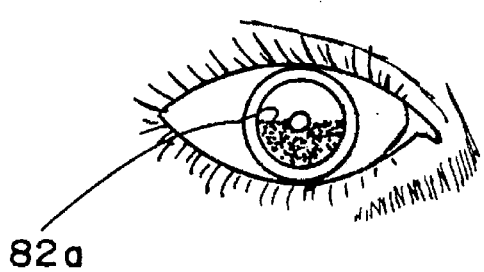
Figure 5:
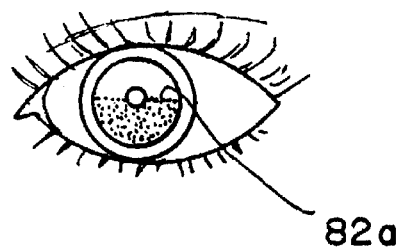
Figure 6:
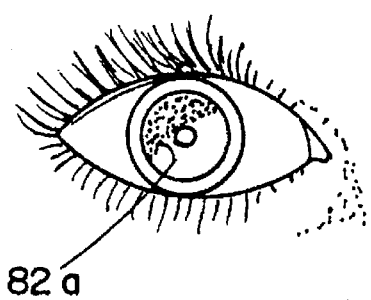
Figure 6:
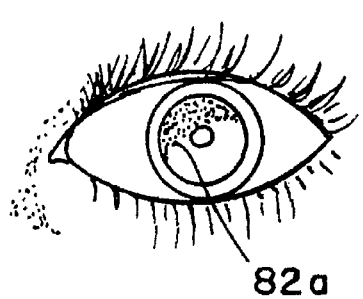

Significantly, the straight edge 68 (FIG. 2) of opaque material 66 across objective 62 is visible in the reflection from the eyes as a horizontal line 82a, as shown in FIGS. 4 and 5. As such, astigmatism, as seen in FIG. 6, which is associated with myopia and hypermetropia, is diagnosed by rotation of the illuminated areas and lines 82a. The direction of rotation correlates with the axis of the astigmatic eye in either a positive or negative direction, with the extent of rotation being a combination of the axis and optical power of the astigmatic eye. Opacities of the eyes, such as cataracts and scars of the cornea (not shown) are evident as dark nebulae and correlate with the position of the cataract. Other types of maladies, such as a detached retina, are generally evident as aberrations in the retinal reflection.

In the instance where adequacy of reflective lenses is to be determined, a subject is entrained to look at the moving light and is photographed as described having the corrective lenses in place. Here, the flash is adjusted so that angular separation between beam 56 and camera lens 74 is slightly less than one degree, wherein the instrument is most sensitive to refractive errors. In the instance where the corrective lenses are adequate, the eyes as seen through the corrective lenses will have the optical signature of normal eyes. Where the corrective lenses are inadequate or too strong, the eyes will have the characteristic pattern of the prevailing refractive error as described.

Figure 7:
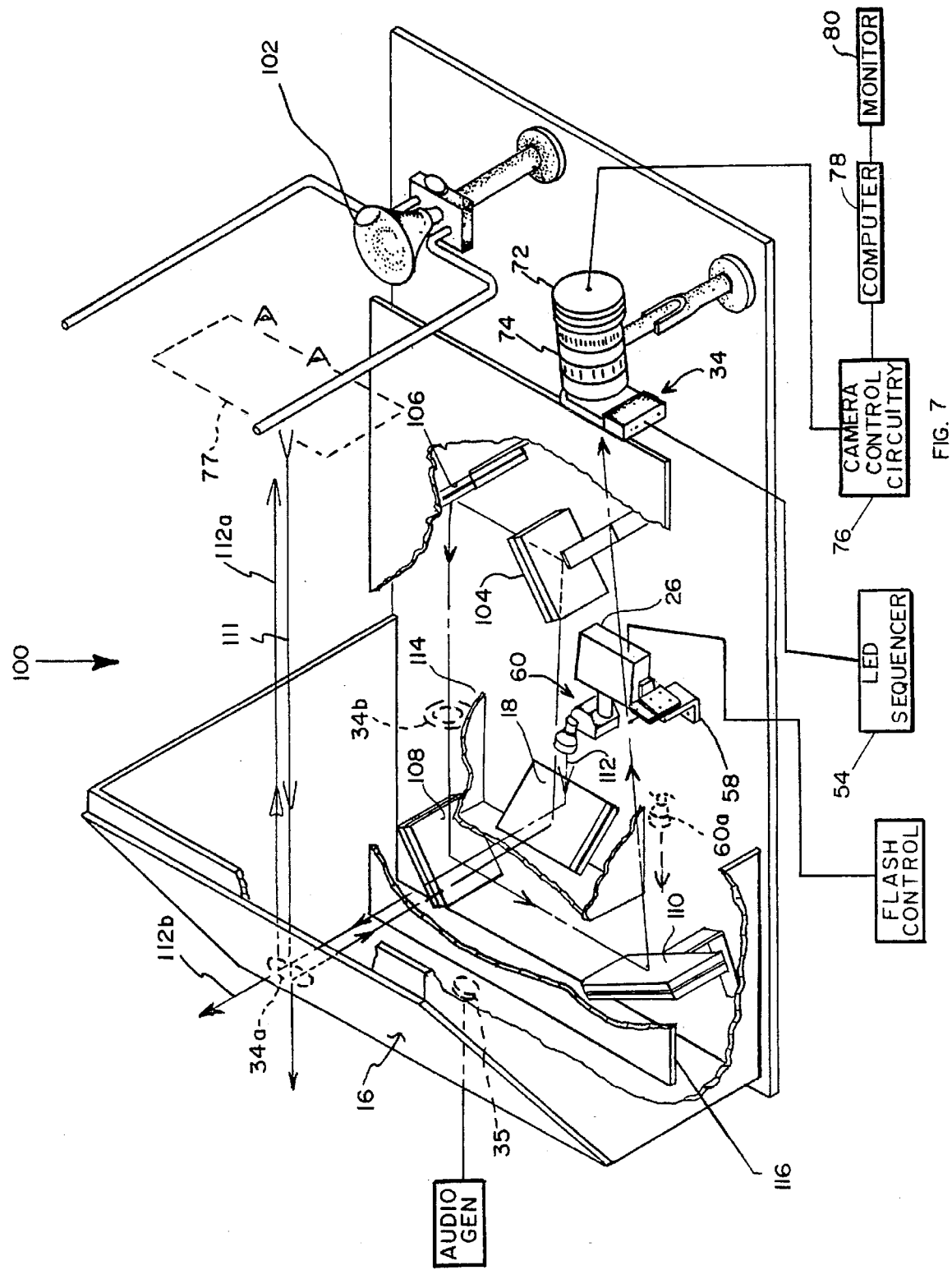
FIG. 7 is a partial pictorial, partial block diagram view partially broken away of a second embodiment of the present invention.

In another embodiment of the invention, as shown in FIG. 7, length of a device 100 constructed in accordance with the principles described above is further shortened to about 24 inches while maintaining a 2 meter focal length of the camera lens. This is accomplished by using a plurality of mirrors to further fold the optical path between the camera and the subject. In this embodiment, flash 26 is constructed as described in the foregoing having a telescopic lens system 60, a focal length thereof being adjustable to produce a beam that is converging, diverging or collimated. However, to produce greater divergence of the beam of light over the shorter distance of the device, the eyepiece and objective of telescopic lens system 60 may be reversed as described, with the objective receiving light from flash 26. Alternately, flash 26 may be mounted to direct the beam of light directly onto the beamsplitter (not shown), which reflects the beam to eyes of a subject, or flash 26 may be mounted as shown at dashed line position 60a wherein a lens of lens system 60 passes the beam to mirror 10. Further, as described, the flash and lens system may be mounted at any point between the chinrest and camera.

Light apparatus 34 is constructed as described above from a ring flash, but is conventionally mounted to the lens of camera 72 as shown in FIG. 7. Here, the difference in focal planes between the light apparatus and the beamsplitter from eyes of a subject is about 61.75 inches. With this greater difference of focal lengths between the beamsplitter and light apparatus 34, it is believed that the defocussing effect which breaks convergence of the eyes is increased. Alternately, apparatus 34 may be located at any point between lens 74 and beamsplitter 16, as illustrated at dashed line position 34b, so as to direct an image of a varying light to mirrors 106, 104, and 18 to beamsplitter 16.

A chinrest 102 is positioned as shown at one end of device 100, with beamsplitter 16 located as shown about 17 inches in front of chinrest 102, and tilted as in the prior embodiment to direct an image downward. Mirror 18 is located about 10 inches below beamsplitter 16, and is tilted so as to receive an image from beamsplitter 16, and also receive a reflection from mirror 104, which is located about 9.75 inches toward chinrest 102 from mirror 18. Mirror 104 in turn is angled to direct and receive a reflection to/from mirror 106, which is about 4.5 inches from mirror 104, which reflection taking a path generally normal to the line of sight to beamsplitter 16 from chinrest 102. Mirror 106 in turn directs and receives a reflection to/from mirror 108, which is about 13.5 inches distant from mirror 106. Mirror 108 directs and receives a reflection to/from mirror 110, about 10 inches distant from mirror 108 and in a plane behind beamsplitter 16. Mirror 110 is positioned to direct an image of eyes of the subject to lens 74 of camera 72 and receive an image from fixation apparatus 34. Constructed as such, the focal length from chinrest 102 to lens 74 is about 78.75 inches, or two meters, the same focal distance as the prior described embodiment of the invention, which has the advantages as described in the foregoing.

Camera 72 and lens 74 are mounted adjacent to chinrest 102, with the lens angled as shown so that lens 74 is directed at mirror 110. Flash 26 is adjustably mounted as described above to direct the beam to beamsplitter 16 by means of adjustable mount 58, which is adjustable as described so that 0–5 degrees of angular separation between an axis of the flash and an axis of the camera lens may be obtained. However, flash 26, if mounted to direct a beam to mirror 110 as described for position 34b, may be tilted to produce divergence of the beam from the retinal reflection to reduce overlap of the beam and retinal reflection on the mirrors, which tends to wash out the image of the retinal reflections. Additionally, when imaging eyes through corrective lenses, the diverging beam from tilted flash 26 impinges the corrective lenses as a slight angle, which otherwise would reflect light back to the camera lens, producing a glare from the corrective lenses. Further, filters may be positioned at the camera and flash and lens system for selectively passing selected wavelengths and/or for selectively blocking or passing polarized light. Also, a second light apparatus 34 or the like may be mounted to a rearward side of beamsplitter 16 to provide a near fixation light for reasons described in the foregoing. An audio stimulation device 35 (dashed lines) is positioned behind beamsplitter 16, and operates as described above.

Vertical baffles 114 serve to separate the light path between the mirrors, while a horizontal baffle 116 having an opening as shown by opening 24 (FIG. 1) separates the light path between beamsplitter 16 and the other mirrors. These baffles block scattered and diffracted light which otherwise may interfere and degrade the images passed between the beamsplitter and mirrors.

Function of this embodiment is similar to the above-described embodiment, which after computer 78 and flash 26 are readied as described, the subject places his/her chin in chinrest 102, which is adjusted as described. The subject, if cooperative, is instructed to look at the moving lights, and if a preverbal child, hears the sound from audio stimulator 35, causing the child to look at the moving lights. The effect of looking at objects in two focal planes causes the eyes to be defocused, bringing the optical axes of the eyes into approximate parallel relation and relaxing the lens structure of the eyes, at which point the flash is activated to produce beam 112 from the telescopic lens system 60 of flash 26. Beam 112 impinges upon beamsplitter 16, which passes a portion of the beam 112a to eyes of the subject, with the other, unused portion of the beam 112b passed to infinity. The reflection ray 111 from the eyes, which includes the retinal reflection and any divergence thereof caused by refractive error defects of the lens structure of the eyes, is passed to beamsplitter 16, which passes the retinal reflection back toward the flash. Camera 72 records the image of the eyes, and computer 78 processes images thereof as described above in accordance with its software, and provides an enhanced image that may be examined in real time or stored for later analysis. Thus, the enhanced image of eyes of the subject is immediately available so a determination may be made as to whether the subject needs corrective measures to improve his/her vision.

Having thus described my invention and the manner of its use, it is apparent that incidental changes and modifications may be made thereto that fairly fall within the scope of the following appended claims, wherein I claim:

We claim:

1. A method implemented by a data processor for analyzing an optical state of a subject's eyes by analyzing light intensity levels of an image of at least one eye of said eyes, said image generated by directing a beam of light into said eyes and registering a reflection of said eyes by a light intensity detector, and comprising the steps of:
   1) locating a pupil of each of said subject's eyes,
   2) analyzing light intensity levels of a retinal reflection from each said pupil to determine whether pathologic conditions are present,
   3) plotting results of an analysis of each said retinal reflection,
   4) displaying a plot of said results.

2. A method as set forth in claim 1 wherein said step of analyzing said light intensity levels of said retinal reflection comprises the step of dividing an image of each said retinal reflection into portions and comparing light intensity levels of each of said portions to a reference.

3. A method as set forth in claim 1 wherein said step of analyzing said light intensity levels of said retinal reflection comprises the step of dividing an image of each said retinal reflection into portions and comparing light intensity levels of a selected said portion with light intensity levels of others of said portions.

4. A method as set forth in claim 1 wherein said step of analyzing said light intensity levels of said retinal reflection comprises the step of comparing light intensity levels of selected points in said retinal reflection to reference light intensity levels.

5. A method as set forth in claim 1 wherein said step of analyzing said light intensity levels of said retinal reflection comprises the step of comparing light intensity levels of selected points in said retinal reflection with other selected points in said retinal reflection.

6. A method as set forth in claim 1 wherein said step of analyzing said light intensity levels of said retinal reflection includes the step of assessing binocular optical status of both said eyes simultaneously.

7. A method as set forth in claim 1 wherein said step 1) thereof further comprises the steps of:
   1) selecting an area of said image of said eye including light intensity levels of said retinal reflection,
   2) superimposing light intensity levels of a reference retinal reflection over a portion of said area,
   3) determining correlation between said light intensity levels of said reference retinal reflection and said light intensity levels of said portion of said area,
   4) moving said reference retinal reflection to a different portion over said area,
   5) repeating steps 3 and 4 until light intensity levels of a said portion of said area having a highest correlation with said light intensity levels of said reference retinal reflection is located.

8. A method as set forth in claim 1 wherein said step 1) thereof further comprises the steps of:
   1) developing a threshold such that said light intensity levels of said retinal reflection are generally above said threshold,
   2) applying said threshold to discrete light intensity levels of said image of said eye,
   3) applying a circular mask to a first position in said area, said mask having a center point and highest correlation when centered over those said light intensity levels of said retinal reflection above said threshold,
   4) testing different positions in said image of said eye with said circular mask until a position of said positions having a highest said correlation with said circular mask is located, and,
   5) identifying an axis of said eye with said center point of said circular mask.

9. A method as set forth in claim 8 further comprising the steps of:
   1) checking light intensity levels of selected points around said retinal reflection in a said position having said highest correlation, for light intensity levels indicative of an iris, and where said light intensity levels do not indicate an iris,
   2) increasing said threshold by a selected amount,
   3) continuing said testing with said circular mask until a said position having a highest said correlation is located wherein said light intensity levels of said selected points are indicative of said iris.

10. A method as set forth in claim 9 further comprising the steps of:
   1) testing said center point in said position having said highest correlation for a light intensity level indicative of a corneal reflection, and if an indication of said corneal reflection is not present,
   2) providing a diagnosis of strabismus.

11. A method as set forth in claim 7 wherein said step 1) thereof further comprises the steps of:
   1) vertically dividing said image of both said eyes into a first portion and a second portion so that a single eye of said eyes is located in a respective one of said first portion and said second portion,
   2) selecting a point indicative of a corneal reflection in each of said first portion and said second portion,
   3) centering a said area on said point indicative of a corneal reflection in said first portion and said second portion.

12. A method as set forth in claim 3 further comprising the steps of:

1) averaging light intensity levels in each said portion,
2) comparing averaged light intensity levels in each said portion with averaged light intensity levels in others of said portions,
3) providing a diagnosis of a normal eye if said averaged light intensity levels in each of said portions are approximately alike.

13. A method as set forth in claim 12 wherein if said averaged light intensity levels are not approximately alike, then further comprising the steps of:

1) averaging light intensity levels of those said portions located in an upper region of said image,
2) averaging light intensity levels of those said portions located in a lower region of said image,
3) comparing an averaged light intensity level of upper said portions with an averaged light intensity level of lower said portions,
4) providing a diagnosis of refractive error of a type including myopia and hyperopia where said upper portions have a higher said averaged light intensity level,
5) providing a diagnosis of refractive error opposite to said refractive error of step 4) where said lower portions have a higher said averaged light intensity level.

14. A method as set forth in claim 12 wherein if said averaged light intensity levels of each said portion are not approximately alike, and one said portion has a significantly higher said averaged light intensity level than others of said portions, then providing a diagnosis including at least one of stigmatism and local defect.

15. A method as set forth in claim 4 further comprising the steps of:

1) selecting a range of focussing powers within which said subject's eyes are deemed to be normal,
2) plotting upper and lower bounds of said range of focussing powers,
3) plotting said light intensity levels of said selected points in a said retinal reflection,
4) superimposing a plot of said light intensity levels of said selected points in a said retinal reflection over a plot of said upper and lower bounds in best fit relation.

16. A method as set forth in claim 15 further comprising the step of deriving said range of focussing powers from a normal retinal reflection.

17. A method as set forth in claim 16 wherein said selected points are selected by steps further comprising:

1) selecting a centrally located, vertically extending region in said retinal reflection,
2) selecting a corresponding centrally located, vertically extending region in said reference.

18. A method as set forth in claim 17 further comprising the steps of:

1) providing an indication of refractive error of a type including myopia and hyperopia where light intensity levels in an upper region of said centrally located region in said retinal reflection are greater than light intensity levels in an upper region of said centrally located region in said reference,
2) providing an indication of refractive error opposite to the indicated refractive error of said step 1) where light intensity levels in a lower region of said centrally located region in said retinal reflection are greater than light intensity levels in a lower region of said centrally located region in said reference.

19. A method as set forth in claim 18 wherein if said light intensity levels of said upper and lower regions of said centrally located region of said retinal reflection are outside said upper and lower bounds, then further comprising the steps of:

1) selecting third and fourth vertically extending regions on left and right sides, respectively, of said center region,
2) determining if light intensity levels of selected points in upper portions of said third and fourth regions are greater than light intensity levels of corresponding points in lower portions of said third and fourth regions, and if so, indicating refractive error of a type including myopia and hyperopia,
3) determining if light intensity levels of points in said upper portions of said third and fourth regions are less than light intensity levels of corresponding points in said lower portions of said third and fourth regions, and if so, indicating refractive error opposite to said refractive error of step 2).

20. A method as set forth in claim 5 further comprising the steps of:

1) locating a center of said retinal reflection,
2) selecting a first annularly positioned plurality of points at a first radius from said center of said retinal reflection,
3) comparing light intensity levels of pairs of those said plurality of points radially opposed across said center of said retinal reflection,
4) selecting a different plurality of annularly positioned points at a different radius than a prior selected said radius,
5) repeating steps 3) and 4) until said annularly positioned points at each said selected radius have been tested,
6) plotting results of compared said intensity levels of each said annularly positioned pairs of points.

21. A method as set forth in claim 20 wherein said step 2 thereof further comprises the step of calculating logarithm of ratio of intensity levels of said pairs of plurality of points radially opposed across said center of said retinal reflection.

22. A method as set forth in claim 1 further comprising the steps of:

1) selecting a point in a said retinal reflection,
2) determining uniformity of light intensity levels between said selected point and all points immediately surrounding said selected point,
3) selecting a different point in said retinal reflection,
4) repeating steps 2) and 3) until all said points in said retinal reflection have been tested,
5) inversely relating optical distortion of a said subject's eyes with said uniformity of light.

23. A method as set forth in claim 22 wherein step 2) thereof further comprises the steps of:

1) establishing an upper limit and a lower limit of acceptable uniformity for each said selected point,
2) determining whether said points surrounding said selected point are within said upper limit and said lower limit.

* * * * *